US010918877B2

(12) United States Patent
Roberto et al.

(10) Patent No.: US 10,918,877 B2
(45) Date of Patent: Feb. 16, 2021

(54) BATTERY LOCK FOR AMBULATORY MEDICAL DEVICE

(71) Applicant: ZOLL MEDICAL CORPORATION, Chelmsford, MA (US)

(72) Inventors: Mark F. Roberto, Pittsburgh, PA (US); John Clark, Pittsburgh, PA (US)

(73) Assignee: ZOLL Medical Corporation, Chelmsford, MA (US)

(*) Notice: Subject to any disclaimer, the term of this patent is extended or adjusted under 35 U.S.C. 154(b) by 190 days.

(21) Appl. No.: 16/145,795

(22) Filed: Sep. 28, 2018

(65) Prior Publication Data
US 2020/0101306 A1 Apr. 2, 2020

(51) Int. Cl.
A61N 1/39 (2006.01)
A61N 1/36 (2006.01)
G16H 20/30 (2018.01)

(52) U.S. Cl.
CPC ....... A61N 1/3968 (2013.01); A61N 1/36135 (2013.01); A61N 1/3975 (2013.01); A61N 1/3904 (2017.08); G16H 20/30 (2018.01)

(58) Field of Classification Search
None
See application file for complete search history.

(56) References Cited

U.S. PATENT DOCUMENTS

| 4,576,170 A | 3/1986 | Bradley et al. |
| 4,580,572 A | 4/1986 | Granek et al. |
| 4,583,547 A | 4/1986 | Granek et al. |
| 4,729,377 A | 3/1988 | Granek et al. |

(Continued)

FOREIGN PATENT DOCUMENTS

| JP | 2002-514107 | 5/2002 |
| JP | 2008-302228 | 12/2008 |

(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/ull/166/1/111.

(Continued)

Primary Examiner — Christopher Koharski
Assistant Examiner — James Moss
(74) Attorney, Agent, or Firm — Finch & Maloney PLLC

(57) ABSTRACT

An ambulatory medical device is provided. The device includes battery lock circuitry configured to transmit a lock signal at a beginning of a battery lock period of the ambulatory medical device and transmit an unlock signal upon detecting an unlock triggering event indicating an end of the battery lock period of the ambulatory medical device. The device also includes a battery being configured to be securely disposed within a chamber of the ambulatory medical device in a first locked manner and provide power to the ambulatory medical device and a battery lock configured to mechanically engage the battery in a second locked manner upon receiving the lock signal indicating the beginning of the battery lock period of the ambulatory medical device and mechanically disengage the battery from the second locked manner upon receiving the unlock signal signaling the end of the battery lock period.

25 Claims, 17 Drawing Sheets

(56) References Cited

U.S. PATENT DOCUMENTS

| | | |
|---|---|---|
| 4,928,690 A | 5/1990 | Heilman et al. |
| 4,991,217 A | 2/1991 | Garrett et al. |
| 5,078,134 A | 1/1992 | Heilman et al. |
| 5,225,763 A | 7/1993 | Krohn et al. |
| 5,306,956 A | 4/1994 | Ikeda et al. |
| 5,606,242 A | 2/1997 | Hull et al. |
| 5,619,117 A | 4/1997 | Koenck |
| 5,625,291 A | 4/1997 | Brink et al. |
| 5,721,482 A | 2/1998 | Benvegar et al. |
| 5,741,306 A | 4/1998 | Glegyak et al. |
| 5,929,601 A | 7/1999 | Kaib et al. |
| 5,944,669 A | 8/1999 | Kaib |
| 6,065,154 A | 5/2000 | Hulings et al. |
| 6,097,982 A | 8/2000 | Glegyak et al. |
| 6,169,387 B1 | 1/2001 | Kaib |
| 6,253,099 B1 | 6/2001 | Oskin et al. |
| 6,280,461 B1 | 8/2001 | Glegyak et al. |
| 6,336,900 B1 | 1/2002 | Alleckson et al. |
| 6,374,138 B1 | 4/2002 | Owen et al. |
| 6,406,426 B1 | 6/2002 | Reuss et al. |
| 6,546,285 B1 | 4/2003 | Owen et al. |
| 6,681,003 B2 | 1/2004 | Linder et al. |
| 6,889,078 B2 | 5/2005 | Struble et al. |
| 6,889,079 B2 | 5/2005 | Bocek et al. |
| 6,908,437 B2 | 6/2005 | Bardy |
| 7,149,579 B1 | 12/2006 | Koh et al. |
| 7,340,296 B2 | 3/2008 | Stahmann et al. |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,712,373 B2 | 5/2010 | Nagle et al. |
| 7,728,548 B2 | 6/2010 | Daynes et al. |
| 7,831,303 B2 | 11/2010 | Rueter et al. |
| 7,974,689 B2 | 7/2011 | Volpe et al. |
| 7,991,460 B2 | 8/2011 | Fischell et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,369,944 B2 | 2/2013 | Macho et al. |
| 8,406,842 B2 | 3/2013 | Kaib et al. |
| 8,644,925 B2 | 2/2014 | Volpe et al. |
| 8,649,861 B2 | 2/2014 | Donnelly et al. |
| 8,706,215 B2 | 4/2014 | Kaib et al. |
| 8,774,917 B2 | 7/2014 | Macho et al. |
| 8,880,196 B2 | 11/2014 | Kaib |
| 8,897,860 B2 | 11/2014 | Volpe et al. |
| 8,904,214 B2 | 12/2014 | Volpe et al. |
| 9,283,399 B2 | 3/2016 | Donnelly et al. |
| 2001/0031991 A1 | 10/2001 | Russial |
| 2003/0004547 A1 | 1/2003 | Owen et al. |
| 2003/0032988 A1 | 2/2003 | Fincke |
| 2003/0095648 A1 | 5/2003 | Kaib et al. |
| 2005/0131465 A1 | 6/2005 | Freeman et al. |
| 2006/0211934 A1 | 9/2006 | Hassonjee et al. |
| 2008/0033495 A1 | 2/2008 | Kumar |
| 2008/0306560 A1 | 12/2008 | Macho et al. |
| 2008/0306562 A1 | 12/2008 | Donnelly et al. |
| 2008/0312709 A1 | 12/2008 | Volpe et al. |
| 2009/0076363 A1 | 3/2009 | Bly et al. |
| 2009/0076559 A1 | 3/2009 | Libbus et al. |
| 2009/0234410 A1 | 9/2009 | Libbus et al. |
| 2009/0264792 A1 | 10/2009 | Mazar |
| 2009/0292194 A1 | 11/2009 | Libbus et al. |
| 2009/0312650 A1 | 12/2009 | Maile et al. |
| 2010/0052892 A1 | 3/2010 | Allen et al. |
| 2010/0069735 A1 | 3/2010 | Berkner |
| 2010/0076533 A1 | 3/2010 | Dar et al. |
| 2010/0298899 A1 | 11/2010 | Donnelly et al. |
| 2010/0312297 A1 | 12/2010 | Volpe et al. |
| 2011/0022105 A9 | 1/2011 | Owen et al. |
| 2011/0093840 A1 | 4/2011 | Pynenburg et al. |
| 2011/0170692 A1 | 7/2011 | Konrad et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2012/0283794 A1 | 11/2012 | Kaib et al. |
| 2012/0289809 A1 | 11/2012 | Kaib et al. |
| 2012/0293323 A1 | 11/2012 | Kaib et al. |
| 2012/0302860 A1 | 11/2012 | Volpe et al. |
| 2013/0013014 A1 | 1/2013 | Donnelly et al. |
| 2013/0060149 A1 | 3/2013 | Song et al. |
| 2013/0085538 A1 | 4/2013 | Volpe et al. |
| 2013/0144355 A1 | 6/2013 | Macho et al. |
| 2013/0218252 A1 | 8/2013 | Kaib et al. |
| 2013/0231711 A1 | 9/2013 | Kaib |
| 2013/0324868 A1 | 12/2013 | Kaib et al. |
| 2013/0325078 A1 | 12/2013 | Whiting et al. |
| 2013/0325096 A1 | 12/2013 | Dupelle et al. |
| 2014/0163334 A1 | 6/2014 | Volpe et al. |
| 2014/0206974 A1 | 7/2014 | Volpe et al. |
| 2014/0277243 A1 | 9/2014 | Maskara et al. |
| 2014/0303680 A1 | 10/2014 | Donnelly et al. |
| 2014/0324112 A1 | 10/2014 | Macho et al. |
| 2015/0035654 A1* | 2/2015 | Kaib ................ H01M 10/48 340/10.51 |
| 2015/0037636 A1 | 2/2015 | Amsler et al. |
| 2015/0039042 A1 | 2/2015 | Amsler et al. |
| 2015/0039053 A1 | 2/2015 | Kaib et al. |
| 2015/0080699 A1 | 3/2015 | Kaib et al. |
| 2015/0224330 A1 | 8/2015 | Kaib et al. |
| 2016/0256161 A1* | 9/2016 | Overmyer ........ A61B 17/07207 |
| 2017/0003356 A1* | 1/2017 | Kaib ................ G01R 31/389 |
| 2017/0296826 A1* | 10/2017 | Whiting .............. A61N 1/046 |
| 2019/0255341 A1* | 8/2019 | Buchanan .......... A61N 1/3904 |

FOREIGN PATENT DOCUMENTS

| | | |
|---|---|---|
| JP | 2008302225 | 12/2008 |
| JP | 2009510631 | 3/2009 |
| WO | 8304171 | 12/1983 |
| WO | 1998039061 | 9/1998 |
| WO | 2004078259 | 9/1998 |
| WO | 2009122277 | 10/2009 |
| WO | 2012006524 | 1/2012 |
| WO | 2012149482 | 11/2012 |
| WO | 2013130957 | 9/2013 |
| WO | 2014097035 | 6/2014 |

OTHER PUBLICATIONS http://web.archive.org/web/20030427001846/http:/www.lifecor.comiimagelib/imageproduct.asp. Published by LifeCor, Inc., 2002, on a webpage owned by LifeCor, Inc.

Association for the Advancement of Medical Instrumentation, ANSI/AAMI DF80:2003 Medical Electrical Equipment—Part 2-4: Particular Requirements for the Safety of Cardiac Defibrillators (including Automated External Defibrillators) 2004, ISBN 1-57020-210-9; abstract; p. vi; p. 50, section 107.1.2.

Zoll Medical Corporation, LifeVest Model WCD 3000 Operator's Manual, Pittsburgh, PA.

Honeywell, "HIH-4000 Series Humidity Sensors", 2010, 6 pages.

* cited by examiner

702

DO YOU WANT TO REMOVE THE BATTERY?

YES   NO

704

ENTER YOUR SECURE PIN

BATTERY LOCK FOR AMBULATORY MEDICAL DEVICE

BACKGROUND

The present disclosure is directed to an ambulatory medical device including an integrated battery lock.

There are a wide variety of electronic and mechanical devices for monitoring and treating patients' medical conditions. In some examples, depending on the underlying medical condition being monitored or treated, medical devices such as cardiac monitors or defibrillators may be surgically implanted or externally attached to the patient. In some cases, physicians may use medical devices alone or in combination with drug therapies to treat conditions such as cardiac arrhythmias.

One of the deadliest cardiac arrhythmias is ventricular fibrillation, which occurs when normal, regular electrical impulses are replaced by irregular and rapid impulses, causing the heart muscle to stop normal contractions. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation (VF), ventricular tachycardia (VT), pulseless electrical activity (PEA), and asystole (heart stops all electrical activity) result in the heart providing insufficient levels of blood flow to the brain and other vital organs for the support of life.

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. Implantable cardioverter/defibrillators (ICDs) or external defibrillators (such as manual defibrillators or automated external defibrillators (AEDs)) have significantly improved the ability to treat these otherwise life-threatening conditions. Such devices operate by applying corrective electrical pulses directly to the patient's heart. Ventricular fibrillation or ventricular tachycardia can be treated by an implanted or external defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns.

A patient at high risk of a cardiac arrhythmia may be prescribed a battery-powered ambulatory monitoring and treatment device such as the ZOLL LifeVest® wearable cardioverter defibrillator available from ZOLL Medical Corporation. In order to provide for constant monitoring and readiness for treatment, the battery should be securely fastened within the device and in optimal working order.

SUMMARY

An ambulatory medical device configured to be worn by a patient is described herein. In certain implementations, the ambulatory medical device includes at least one physiological sensor configured to couple to the patient, physiological signal circuitry operably connected to the at least one physiological sensor and configured to receive a physiological signal from the at least one physiological sensor and produce a physiological metric based upon the received physiological signal, therapy delivery circuitry configured to produce a therapy shock based upon the physiological metric, battery lock circuitry configured to transmit a lock signal at a beginning of a battery lock period of the ambulatory medical device and transmit an unlock signal upon detecting an unlock triggering event indicating an end of the battery lock period of the ambulatory medical device, a battery being configured to be securely disposed within a chamber of the ambulatory medical device in a first locked manner and provide power to the ambulatory medical device, and a battery lock configured to mechanically engage the battery in a second locked manner upon receiving the lock signal indicating the beginning of the battery lock period of the ambulatory medical device and mechanically disengage the battery from the second locked manner upon receiving the unlock signal signaling the end of the battery lock period.

In certain implementations of the above ambulatory medical device, the ambulatory medical device also includes a motion sensor in communication with the battery lock circuitry and configured to produce a motion signal of the patient, wherein the battery lock circuitry is configured to transmit at least one of the lock signal and the unlock signal in response to the motion signal. In some examples, the motion signal indicates a patient fall event. In some other examples, the battery lock circuitry is configured to determine the patient fall event based upon the motion signal transgressing a threshold value associated with a fall event. In some additional examples, the motion signal indicates an end of the patient fall event, and the battery lock circuitry is further configured to transmit the unlock signal in response to the end of the patient fall event. In some additional examples, the motion signal indicates a beginning of a physical activity event and an end of the physical activity event. In some additional examples, the battery lock circuitry is further configured to determine the beginning of the physical activity event and the end of the physical activity event from the motion signal, transmit the lock signal in response to the beginning of the physical activity event, and transmit the unlock signal in response to the end of the physical activity event.

In certain implementations of the above ambulatory medical device, the ambulatory medical device also includes a humidity sensor in communication with the battery lock circuitry and configured to produce a humidity signal. In some examples, the battery lock circuitry is configured to transmit at least one of the lock signal and the unlock signal in response to the humidity signal.

In certain implementations of the above ambulatory medical device, the ambulatory medical device also includes a moisture sensor in communication with the battery lock circuitry and configured to produce a moisture signal. In some examples, the battery lock circuitry is configured to transmit at least one of the lock signal and the unlock signal in response to the moisture signal. In some examples, the ambulatory medical device also includes at least one sealing mechanism configured to protect the device from water ingress. In some examples, the at least one sealing mechanism includes an actuatable gasket configured to be engaged to seal one or more water-sensitive portions of the device when the battery is in the second locked manner.

In certain implementations of the above ambulatory medical device, the battery lock circuitry is further configured to monitor a health status of the battery and transmit at least one of the lock signal and the unlock signal in response to the health status. In some examples, the battery lock circuitry is further configured to transmit the unlock signal in response to determining that the health status indicates that the battery satisfies at least one of: has a current charge that is below a charge threshold, is unable to output a current above a predetermined current threshold level, has failed a battery integrity test, and has reached end of life.

In certain implementations of the above ambulatory medical device, the unlock triggering event includes at least one of a change in operation of the ambulatory medical device, a change to the physiological metric, a patient input, and a caregiver input. In some examples, the battery lock circuitry is further configured to transmit the unlock signal upon detecting an unlock triggering event indicating the end of the battery lock period of the ambulatory medical device and determining the ambulatory medical device is not operating in a critical operational period.

In certain implementations of the above ambulatory medical device, the at least one physiological sensor includes an ECG sensor configured to detect one or more ECG signals of the patient. In some examples, the physiological metric includes at least one ECG metric.

In certain implementations of the above ambulatory medical device, the battery lock includes at least one of a solenoid, a motor rotatably connected to a reciprocating shaft, and a user-actuated locking mechanism.

In certain implementations of the above ambulatory medical device, the battery includes a recessed portion configured to receive at least a portion of the battery lock.

In certain implementations of the above ambulatory medical device, the battery includes at least a portion of the battery lock circuitry. In some examples, the battery further includes the battery lock. In some examples, the chamber of the ambulatory medical device includes a recessed portion configured to receive at least a portion of the battery lock.

An alternative ambulatory medical device to be worn by a patient is also described herein. The alternative ambulatory medical device includes at least one physiological sensor configured to couple to the patient, physiological signal circuitry operably connected to the at least one physiological sensor and configured to receive a physiological signal from the at least one physiological sensor and produce a physiological metric based upon the received physiological signal, therapy delivery circuitry configured to produce a therapy shock based upon the physiological metric, battery lock circuitry configured to transmit a lock signal at a beginning of a critical operational period of the ambulatory medical device and transmit an unlock signal at an end of the critical operational period of the ambulatory medical device, a battery configured to be securely located within a chamber of the ambulatory medical device in a first secure manner and provide power to the ambulatory medical device, and a battery lock configured to mechanically engage the battery in a second secure manner upon receiving the lock signal indicating the beginning of the critical operational period of the ambulatory medical device and mechanically disengage the battery from the second secure manner upon receiving the unlock signal signaling the end of the critical operational period.

In certain implementations of the above alternative ambulatory medical device, the critical operational period includes the therapy delivery circuitry delivering a therapy shock to the patient.

In certain implementations of the above alternative ambulatory medical device, the critical operational period includes an alarm output by the ambulatory medical device, the alarm indicative of a pending therapeutic shock.

In certain implementations of the above alternative ambulatory medical device, the end of the critical operational period includes at least one of a change in operation of the ambulatory medical device, a change to the physiological metric, a patient input, and a caregiver input. In some examples, the battery lock circuitry is further configured to transmit the unlock signal upon detecting an unlock triggering event indicating the end of the critical operational period of the ambulatory medical device.

In certain implementations of the above alternative ambulatory medical device, the at least one physiological sensor includes an ECG sensor configured to detect one or more ECG signals of the patient. In some examples, the physiological metric includes at least one ECG metric.

In certain implementations of the above alternative ambulatory medical device, the battery lock includes at least one of a solenoid, a motor rotatably connected to a reciprocating shaft, and a user-actuated locking mechanism.

In certain implementations of the above alternative ambulatory medical device, the battery includes a recessed portion configured to receive at least a portion of the battery lock.

In certain implementations of the above alternative ambulatory medical device, the battery includes at least a portion of the battery lock circuitry. In some examples, the battery also includes the battery lock. In some examples, the chamber of the ambulatory medical device includes a recessed portion configured to receive at least a portion of the battery lock.

A method for securing a battery in an ambulatory medical device to be worn by a patient is also described herein. The method includes acts of determining, by battery lock circuitry, a beginning of a locked period of the ambulatory medical device; transmitting, by the battery lock circuitry, a lock signal to a battery lock operably connected to the battery lock circuitry in response to determining the beginning of the locked period of the ambulatory medical device; receiving, by the battery lock, the lock signal; mechanically engaging, by the battery lock, the battery secured in a first secure manner in a chamber of the ambulatory medical device to additionally secure the battery in a second secure manner in response to the lock signal; detecting, by the battery lock circuitry, an end of the locked period of the ambulatory medical device; transmitting, by the battery lock circuitry, an unlock signal in response to detecting the end of the locked period of the ambulatory medical device; receiving, by the battery lock, the unlock signal; and mechanically disengaging, by the battery lock, the battery from the second secure manner.

In certain implementations of the above method, the battery lock includes at least one of a solenoid, a motor rotatably connected to a reciprocating shaft, and a user-actuated locking mechanism.

In certain implementations of the above method, the battery includes a recessed portion configured to receive at least a portion of the battery lock.

In certain implementations of the above method, the battery includes at least a portion of the battery lock circuitry. In some examples, the battery also includes the battery lock. In some examples, the chamber includes a recessed portion configured to receive at least a portion of the battery lock.

A second alternative ambulatory medical device configured to be worn by a patient is also described herein. The second alternative ambulatory medical device includes at least one physiological sensor configured to couple to the patient, physiological signal circuitry operably connected to the at least one physiological sensor and configured to receive a physiological signal from the at least one physiological sensor and produce a physiological metric based upon the received physiological signal, battery lock circuitry configured to transmit an unlock signal upon detecting an unlock triggering event, a battery configured to be securely disposed within a chamber of the ambulatory medical device in a first locked manner and provide power to the ambulatory medical device, and a battery lock configured to mechanically engage the battery in a second locked manner and mechanically disengage the battery from the second locked manner upon receiving the unlock signal.

In certain implementations of the above second alternative ambulatory medical device, the second alternative ambulatory medical device further includes a motion sensor in communication with the battery lock circuitry and configured to produce a motion signal of the patient, wherein the battery lock circuitry is configured to transmit the unlock signal in response to the motion signal. In some examples, the motion signal indicates a patient fall event. In some examples, the battery lock circuitry is configured to determine the patient fall event based upon the motion signal transgressing a threshold value associated with a fall event. In some examples, the motion signal indicates an end of the patient fall event, and the battery lock circuitry is further configured to transmit the unlock signal in response to the end of the patient fall event.

In certain implementations of the above second alternative ambulatory medical device, the motion signal indicates a beginning of a physical activity event and an end of the physical activity event. In some examples, the battery lock circuitry is further configured to determine the beginning of the physical activity event and the end of the physical activity event from the motion signal, transmit a lock signal to mechanically engage the battery in the second locked manner in response to the beginning of the physical activity event, and transmit the unlock signal in response to the end of the physical activity event.

In certain implementations of the above second alternative ambulatory medical device, the second alternative ambulatory medical device further includes a humidity sensor in communication with the battery lock circuitry and configured to produce a humidity signal. In some examples, the battery lock circuitry is configured to transmit at least one of a lock signal to mechanically engage the battery in the second locked manner and the unlock signal in response to the humidity signal.

In certain implementations of the above second alternative ambulatory medical device, the second alternative ambulatory medical device further includes a moisture sensor in communication with the battery lock circuitry and configured to produce a moisture signal. In some examples, the battery lock circuitry is configured to transmit at least one of a lock signal to mechanically engage the battery in the second locked manner and the unlock signal in response to the moisture signal. In some examples, the second alternative ambulatory medical device also includes at least one sealing mechanism configured to protect the device from water ingress. In some examples, the at least one sealing mechanism includes an actuatable gasket configured to be engaged to seal one or more water-sensitive portions of the device when the battery is in the second locked manner.

In certain implementations of the above second alternative ambulatory medical device, the battery lock circuitry is further configured to monitor a health status of the battery and transmit at least one of a lock signal to mechanically engage the battery in the second locked manner and the unlock signal in response to the health status. In some examples, the battery lock circuitry is further configured to transmit the unlock signal in response to determining that the health status indicates that the battery satisfies at least one of: has a current charge that is below a charge threshold, is unable to output a current above a predetermined current threshold level, has failed a battery integrity test, and has reached end of life.

In certain implementations of the above second alternative ambulatory medical device, the unlock triggering event includes at least one of a change in operation of the ambulatory medical device, a change to the physiological metric, a patient input, and a caregiver input. In some examples, the battery lock circuitry is further configured to transmit the unlock signal upon detecting the unlock triggering event and further determining the ambulatory medical device is not operating in a critical operational period.

In certain implementations of the above second alternative ambulatory medical device, the at least one physiological sensor includes an ECG sensor configured to detect one or more ECG signals of the patient. In some examples, the physiological metric includes at least one ECG metric.

In certain implementations of the above second alternative ambulatory medical device, the battery lock includes at least one of a solenoid, a motor rotatably connected to a reciprocating shaft, and a user-actuated locking mechanism.

In certain implementations of the above second alternative ambulatory medical device, the battery includes a recessed portion configured to receive at least a portion of the battery lock.

In certain implementations of the above second alternative ambulatory medical device, the battery includes at least a portion of the battery lock circuitry. In some examples, the battery further includes the battery lock.

An alternative method for securing a battery in an ambulatory medical device to be worn by a patient is also described herein. The alternative method includes the acts of mechanically engaging, by a battery lock, a battery that has been secured in a first secure manner in a chamber of the ambulatory medical device to additionally secure the battery in a second secure manner; detecting, by battery lock circuitry, an unlock triggering event; transmitting, by the battery lock circuitry, an unlock signal in response to detecting the unlock triggering event; receiving, by the battery lock, the unlock signal; and mechanically disengaging, by the battery lock, the battery from the second secure manner.

In certain implementations of the above alternative method, the battery lock includes at least one of a solenoid, a motor rotatably connected to a reciprocating shaft, and a user-actuated locking mechanism.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

FIG. 7 depicts a sample screenshot of a user interface, in accordance with an example of the present disclosure.

DETAILED DESCRIPTION

Overview

Figure 1A:
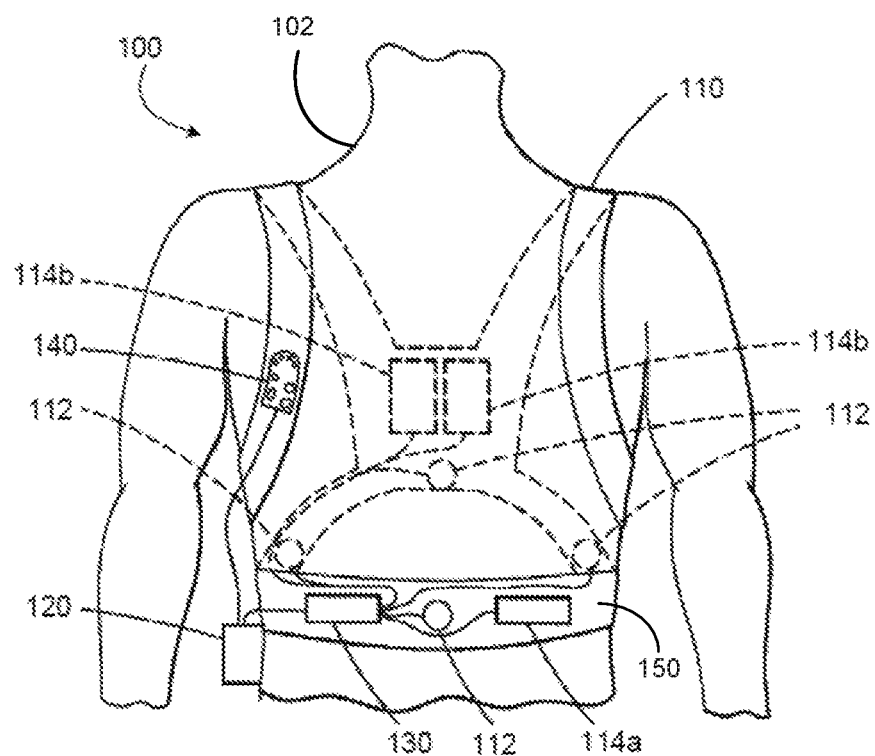
FIGS. 1A-1D depict sample wearable medical devices, in accordance with one or more examples of the present disclosure.

Patient monitoring and treatment devices are often used to monitor and record various physiological or vital signals for a patient and provide treatment to a patient when necessary. For some patients at risk of a cardiac arrhythmia, specialized electrocardiogram (ECG) monitoring and/or treatment devices such as a cardiac event monitoring device, a wearable cardioverter defibrillator (WCD), or a hospital wearable defibrillator can be prescribed to and worn by the patient for a period of time. For example, a patient having an elevated risk of sudden cardiac death, unexplained syncope, prior symptoms of heart failure, an ejection fraction of less than 45%, and other similar patients in a state of degraded cardiac health can be prescribed a specialized device.

For example, a wearable cardioverter defibrillator device, such as the LifeVest® Wearable Cardioverter Defibrillator from ZOLL Medical Corporation (Chelmsford, Mass.), can be prescribed to the patient. As described in further detail below, such a device includes a garment that is configured to be worn about the torso of the patient. The garment can be configured to house various components such as ECG sensing electrodes and therapy electrodes. The components in the garment can be operably connected to a monitoring device that is configured to receive and process signals from the ECG sensing electrodes to determine a current cardiac condition of the patient and, if necessary, provide treatment to the patient using the therapy electrodes.

In various scenarios relevant to this disclosure, in order to provide maximum mobility, the ambulatory medical devices as described herein can be powered by one or more replaceable batteries. The batteries can be configured to be removed, recharged, and replaced on a regular basis (e.g., every 24 hours). However, to ensure constant monitoring and treatment potential, the battery should remain surely affixed and locked in the ambulatory medical device when the device is being worn by the patient.

To remove a battery from an ambulatory medical device, there may be some physical activity or movement associated with removing the battery from the device. For example, the battery can include a push button or other similar attachment/detachment mechanism that is configured to releasably engage one or more receiving components within, for example, a battery receiving recess in the ambulatory medical device. For example, the battery receiving recess can be positioned at a certain location and/or within a specific chamber of the ambulatory medical device. Upon insertion of the battery into the battery receiving recess, the attachment/detachment mechanism can engage the one or more receiving components. The ambulatory medical device can be designed to be worn by patients having limited mobility or strength and, as such, the attachment/detachment mechanism can be designed to be operated with minimal strength or effort to release. However, such a design can limit the locking strength of the battery and certain non-routine events such as sharp impacts on the ambulatory medical device (for example, because of a patient fall) can result in the battery dislodging from the battery receiving recess.

The present disclosure relates to an ambulatory medical device that includes battery lock circuitry that is configured to transmit a lock signal at a beginning of a battery lock period of the ambulatory medical device and to transmit an unlock signal at the end of the battery lock period. The ambulatory medical device can further include a battery lock configured to mechanically engage the battery in a second locked state or manner (e.g., in addition to the attachment/detachment mechanism as described above) in response to the transmitted lock signal. The battery lock can be further configured to mechanically disengage the battery in response to the transmitted unlock signal.

The battery lock period as described herein can vary depending upon the implementation of the ambulatory medical device. In certain implementations, the battery lock period can be associated with a period of critical operation of the ambulatory medical device. For example, if the ambulatory medical device is a WCD, the battery lock period can be any time the patient is wearing the device and the device is monitoring the patient for an adverse cardiac event such as a cardiac arrhythmia. In certain implementations, the battery lock period can be limited to times when the device is preparing to provide a treatment to the patient. Additional battery lock periods are described below in additional detail.

Such an approach provides several advantages over the existing techniques. For example, by providing a second mechanical lock for engaging the battery, accidental battery displacement (whether intentional or unintentional) is avoided. For example, a WCD can provide an audible alarm prior to providing treatment. A patient, or a bystander near a patient, may attempt to the silence the alarm thinking it is a false notification. If unable to silence the alarm using other means, the battery may be removed from the device to ultimately silence the alarm. Such an action can prevent the device from providing a treatment to the patient, resulting in serious patient injury or potentially patient death.

Further, the battery lock approach as described herein provides additional benefits. In certain implementations, the ambulatory medical device can include additional sensors such as motion sensors (e.g., accelerometers) and/or environmental sensors (e.g., humidity and moisture sensors). Such additional sensors can be configured to provide additional locking functionality. For example, an accelerometer can detect that a patient is falling. In response to a fall detection, the battery lock circuitry can transmit a battery lock signal to the battery lock, thereby locking the battery into the medical device in a secondary manner. This secondary lock can reduce or eliminate the potential detachment of the battery because of the fall.

Similarly, in certain implementations, the additional sensors can be configured to work with the battery lock circuitry to further protect various components of the ambulatory medical device. For example, if a humidity sensor detects an increase in humidity, the battery lock circuitry can transmit a battery lock signal to the battery lock. The battery and/or the battery recess in the ambulatory medical device can include, for example, a gasket or other similar waterproof barrier or membrane that is configured to form a watertight seal between the battery and the battery recess when locked in the secondary manner.

These examples, and various other similar examples of benefits and advantages of the techniques, processes, and approaches as provided herein, are described in additional detail below.

Example Devices with Batter Lock Features

The teachings of the present disclosure can be generally applied to external medical monitoring and/or treatment devices. Such external medical devices can include, for example, ambulatory medical devices that are capable of and designed for moving with the patient as the patient goes about his or her daily routine. An example ambulatory medical device can be a wearable medical device such as a wearable cardioverter defibrillator (WCD), a wearable cardiac monitoring device, an in-hospital device such as an in-hospital wearable defibrillator (HWD), a short-term wearable cardiac monitoring and/or therapeutic device, mobile cardiac event monitoring devices, and other similar wearable medical devices.

The wearable medical device can be capable of continuous use by the patient. In some implementations, the continuous use can be substantially or nearly continuous in nature. That is, the wearable medical device can be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless be considered continuous use. For example, the wearable medical device can be configured to be worn by a patient for as many as 24 hours a day. In some implementations, the patient can remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other caregiver provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., electrocardiogram (ECG) information, including arrhythmia information, cardio-vibrations, etc.) and/or non-cardiac information (e.g., blood oxygen, the patient's temperature, glucose levels, tissue fluid levels, and/or lung vibrations). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. For example, the wearable medical device can be configured to monitor, for example, pulmonary-vibrations (e.g., using microphones and/or accelerometers), breath vibrations, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the wearable medical devices described herein can be pacing-enabled, e.g., capable of providing therapeutic pacing pulses to the patient.

FIG. 1A illustrates an example medical device 100 that is external, ambulatory, and wearable by a patient 102, and configured to implement one or more configurations described herein. For example, the medical device 100 can be a non-invasive medical device configured to be located substantially external to the patient. Such a medical device 100 can be, for example, an ambulatory medical device that is capable of and designed for moving with the patient as the patient goes about his or her daily routine. For example, the medical device 100 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 100 can include one or more of the following: a garment 110, one or more sensing electrodes 112 (e.g., ECG electrodes), one or more therapy electrodes 114a and 114b (collectively referred to herein as therapy electrodes 114), a medical device controller 120, a connection pod 130, a patient interface pod 140, a belt 150, or any combination of these. In some examples, at least some of the components of the medical device 100 can be configured to be affixed to the garment 110 (or in some examples, permanently integrated into the garment 110), which can be worn about the patient's torso.

The medical device controller 120 can be operatively coupled to the sensing electrodes 112, which can be affixed to the garment 110, e.g., assembled into the garment 110 or removably attached to the garment, e.g., using hook and loop fasteners. In some implementations, the sensing electrodes 112 can be permanently integrated into the garment 110. The medical device controller 120 can be operatively coupled to the therapy electrodes 114. For example, the therapy electrodes 114 can also be assembled into the garment 110, or, in some implementations, the therapy electrodes 114 can be permanently integrated into the garment 110.

Component configurations other than those shown in FIG. 1 are possible. For example, the sensing electrodes 112 can be configured to be attached at various positions about the body of the patient 102. The sensing electrodes 112 can be operatively coupled to the medical device controller 120 through the connection pod 130. In some implementations, the sensing electrodes 112 can be adhesively attached to the patient 102. In some implementations, the sensing electrodes 112 and at least one of the therapy electrodes 114 can be included on a single integrated patch and adhesively applied to the patient's body.

The sensing electrodes 112 can be configured to detect one or more cardiac signals. Examples of such signals include ECG signals and/or other sensed cardiac physiological signals from the patient. In certain examples, the sensing electrodes 112 can include additional components such as accelerometers, acoustic signal detecting devices, and other measuring devices for recording additional parameters. For example, the sensing electrodes 112 can also be configured to detect other types of patient physiological parameters and acoustic signals, such as tissue fluid levels, cardio-vibrations, lung vibrations, respiration vibrations, patient movement, etc. Example sensing electrodes 112 include a metal electrode with an oxide coating such as tantalum pentoxide electrodes, as described in, for example, U.S. Pat. No. 6,253,099 titled "Cardiac Monitoring Electrode Apparatus and Method," the content of which is hereby incorporated herein by reference in its entirety.

In some examples, the therapy electrodes 114 can also be configured to include sensors configured to detect ECG signals as well as other physiological signals of the patient. The connection pod 130 can, in some examples, include a signal processor configured to amplify, filter, and digitize these cardiac signals prior to transmitting the cardiac signals to the medical device controller 120. One or more of the therapy electrodes 114 can be configured to deliver one or more therapeutic defibrillating shocks to the body of the patient 102 when the medical device 100 determines that such treatment is warranted based on the signals detected by the sensing electrodes 112 and processed by the medical device controller 120. Example therapy electrodes 114 can include conductive metal electrodes such as stainless-steel electrodes that include one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 114 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) or a patient. Alternatively, the optional therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Figure 1B:
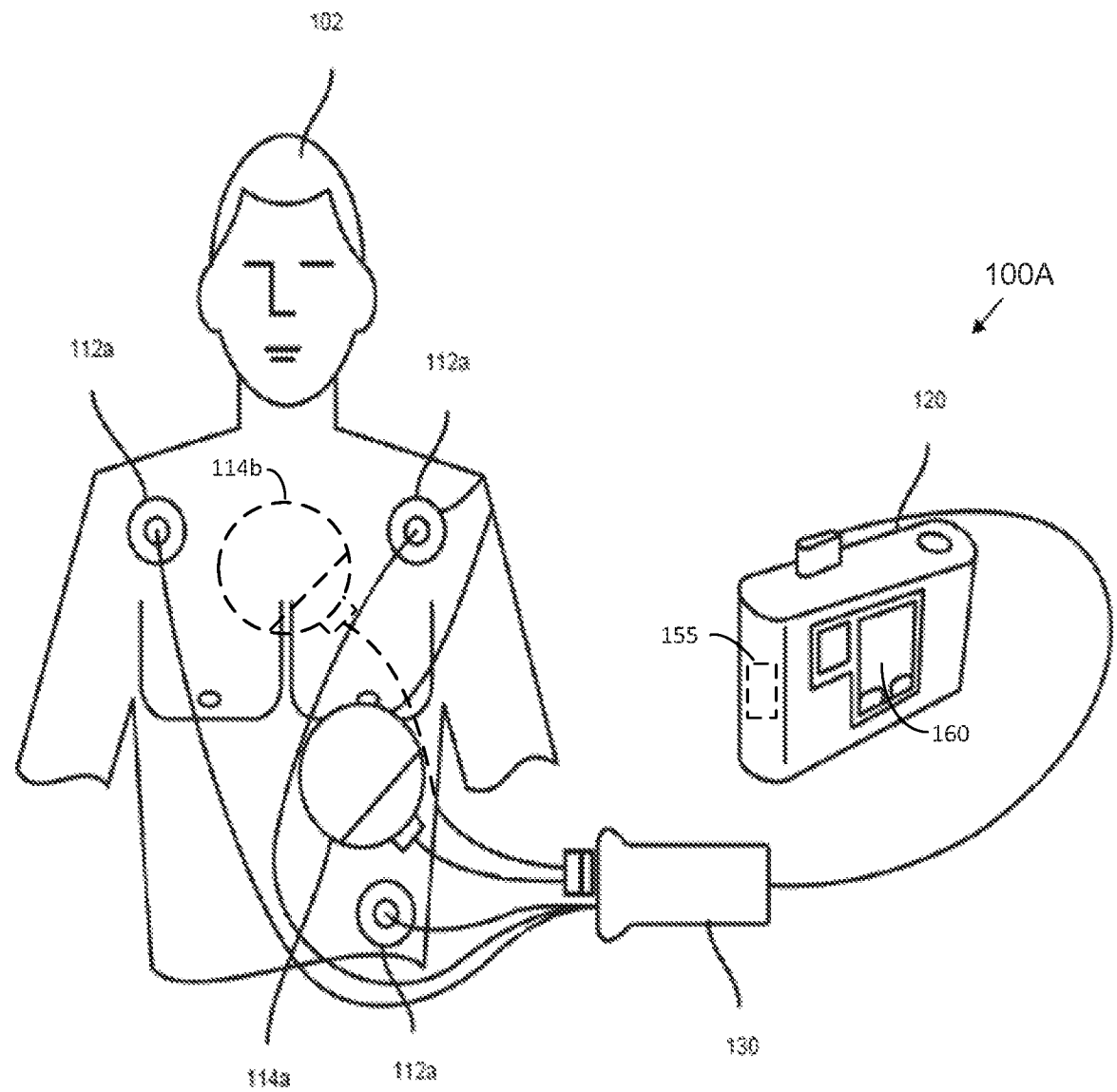

FIG. 1B illustrates a hospital wearable defibrillator 100A that is external, ambulatory, and wearable by a patient 102, and includes a battery locking mechanism 155 in accordance with the systems and methods described herein. Hospital wearable defibrillator 100A can be configured in some implementations to provide pacing therapy, e.g., to treat bradycardia, tachycardia, and asystole conditions. The device 100A can include one or more sensing electrodes 112a, one or more therapy electrodes 114a and 114b, a medical device controller 120 and a connection pod 130. For example, each of these components can be structured and function as like number components of the medical device 100. For example, the electrodes 112a, 114a, 114b can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. For example, the front adhesively attachable therapy electrode 114a attaches to the front of the patient's torso to deliver pacing or defibrillating therapy. Similarly, the back adhesively attachable therapy electrode 114b attaches to the back of the patient's torso. In an example scenario, at least three ECG adhesively attachable sensing electrodes 112a can be attached to at least above the patient's chest near the right arm, above the patient's chest near the left arm, and towards the bottom of the patient's chest in a manner prescribed by a trained professional.

A patient being monitored by a hospital wearable defibrillator and/or pacing device may be confined to a hospital bed or room for a significant amount of time (e.g., 75% or more of the patient's stay in the hospital). As a result, a user interface 160 can be configured to interact with a user other than the patient, e.g., a nurse, for device-related functions such as initial device baselining, setting and adjusting patient parameters, and changing the device batteries.

In some implementations, an example of a therapeutic medical device that includes a battery locking mechanism in accordance with the systems and methods described herein can include a short-term defibrillator and/or pacing device. For example, such a short-term device can be prescribed by a physician for patients presenting with syncope. A wearable defibrillator can be configured to monitor patients presenting with syncope by, e.g., analyzing the patient's physiological and cardiac activity for aberrant patterns that can indicate abnormal physiological function. For example, such aberrant patterns can occur prior to, during, or after the onset of syncope. In such an example implementation of the short-term wearable defibrillator, the electrode assembly can be adhesively attached to the patient's skin and have a similar configuration as the hospital wearable defibrillator described above in connection with FIG. 1A.

Figure 1C:
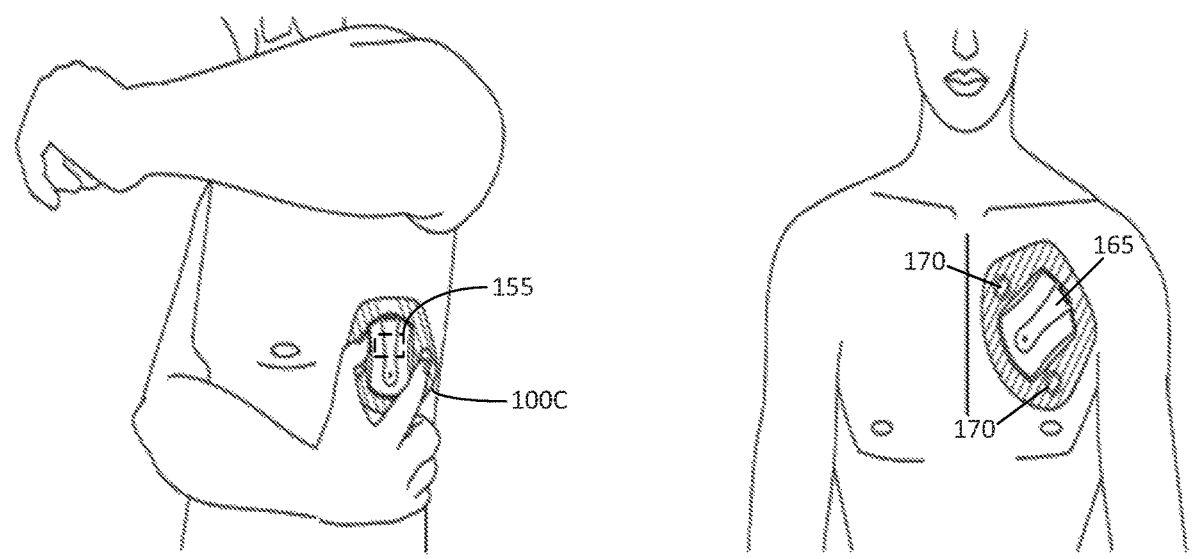
Figure 1D:
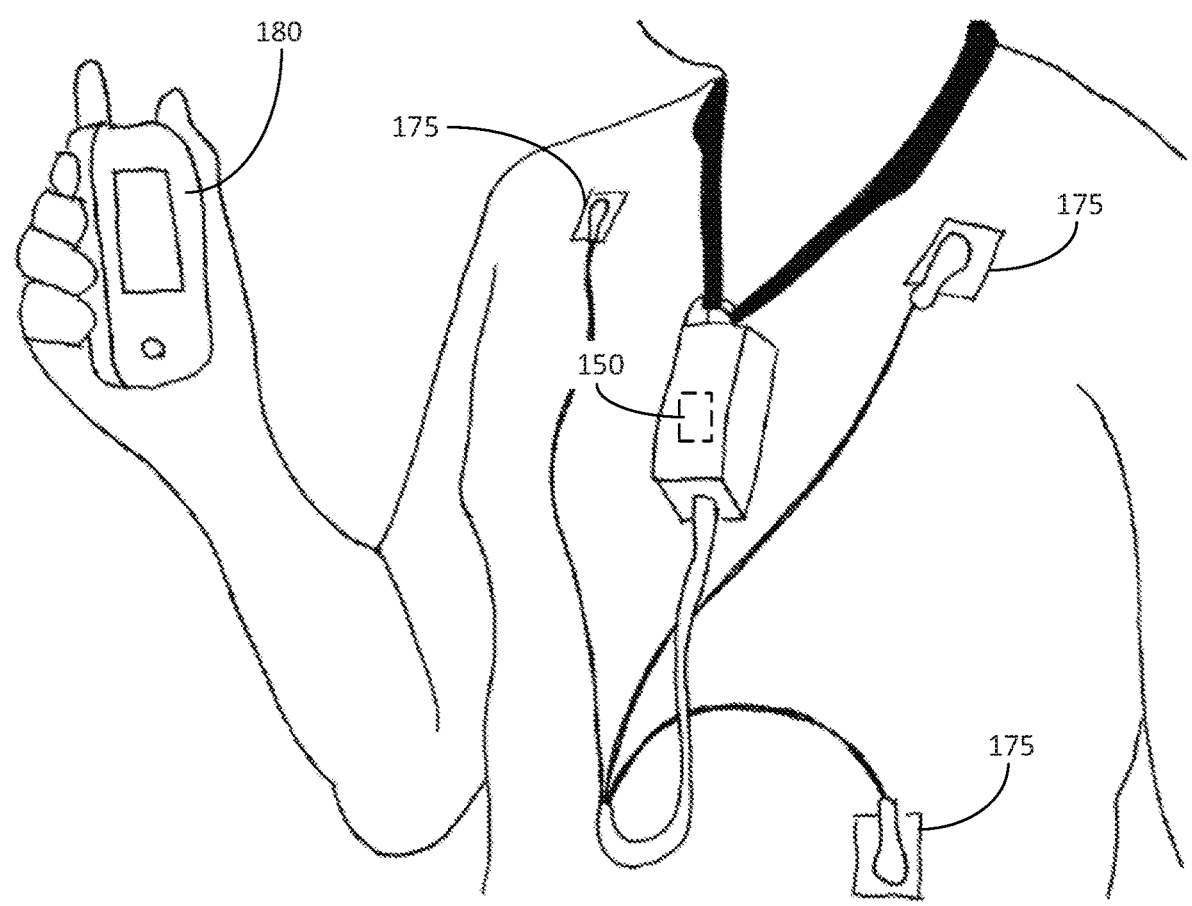

FIGS. 1C and 1D illustrate example wearable patient monitoring devices with no treatment or therapy functions, and which include respective battery locking mechanisms 155 in accordance with the systems and methods described herein. For example, such devices are configured to monitor one or more physiological parameters of a patient, e.g., for remotely monitoring and/or diagnosing a condition of the patient. For example, such physiological parameters can include a patient's ECG information, tissue (e.g., lung) fluid levels, cardio-vibrations (e.g., using accelerometers or microphones), and other related cardiac information. A cardiac monitoring device is a portable device that the patient can carry around as he or she goes about their daily routine.

Referring to FIG. 1C, an example wearable patient monitoring device 100C can include tissue fluid monitors 165 that use radio frequency (RF) based techniques to assess fluid levels and accumulation in a patient's body tissue. Such tissue fluid monitors 165 can be configured to measure fluid content in the lungs, typically for diagnosis and follow-up of pulmonary edema or lung congestion in heart failure patients. The tissue fluid monitors 165 can include one or more antennas configured to direct RF waves through a patient's tissue and measure output RF signals in response to the waves that have passed through the tissue. In certain implementations, the output RF signals include parameters indicative of a fluid level in the patient's tissue. In examples, device 100C may be a cardiac monitoring device that also includes ECG electrodes 170 for sensing ECG activity of the patient. Device 100C can pre-process the ECG signals via one or more ECG processing and/or conditioning circuits such as an analog-to-digital converter, operational amplifiers, digital filters, signal amplifiers under control of a microcontroller. Device 100C can transmit information descriptive of the ECG activity and/or tissue fluid levels via a network interface to a remote server for analysis.

Referring to FIG. 1D, another example wearable cardiac monitoring device 100D that includes a battery locking mechanism 150 can be attached to a patient via at least three adhesive cardiac sensing electrodes 175 disposed about the patient's torso. Cardiac devices 100C and 100D are used in cardiac telemetry and/or continuous cardiac event monitoring applications, e.g., in patient populations reporting irregular cardiac symptoms and/or conditions. These devices can transmit information descriptive of the ECG activity and/or tissue fluid levels via a network interface to a remote server for analysis. Example cardiac conditions that can be monitored include atrial fibrillation (AF), bradycardia, tachycardia, atrio-ventricular block, Lown-Ganong-Levine syndrome, atrial flutter, sino-atrial node dysfunction, cerebral ischemia, pause(s), and/or heart palpitations. For example, such patients may be prescribed a cardiac monitoring for an extended period of time, e.g., 10 to 30 days, or more. In some mobile cardiac telemetry applications, a portable cardiac monitoring device can be configured to substantially continuously monitor the patient for a cardiac anomaly, and when such an anomaly is detected, the monitor can automatically send data relating to the anomaly to a remote server. The remote server may be located within a 24-hour manned monitoring center, where the data is interpreted by qualified, cardiac-trained reviewers and/or caregivers, and feedback provided to the patient and/or a designated caregiver via detailed periodic or event-triggered reports. In certain cardiac event monitoring applications, the cardiac monitoring device is configured to allow the patient to manually press a button on the cardiac monitoring device to report a symptom. For example, a patient can report symptoms such as a skipped beat, shortness of breath, light headedness, racing heart rate, fatigue, fainting, chest discomfort, weakness, dizziness, and/or giddiness. The cardiac monitoring device can record predetermined physiologic parameters of the patient (e.g., ECG information) for a predetermined amount of time (e.g., 1-30 minutes before and 1-30 minutes after a reported symptom). As noted above, the cardiac monitoring device can be configured to monitor physiologic parameters of the patient other than cardiac related parameters. For example, the cardiac monitoring device can be configured to monitor, for example, cardio-vibrational signals (e.g., using accelerometers or microphones), pulmonary-vibrational signals, breath vibrations, sleep related parameters (e.g., snoring, sleep apnea), tissue fluids, among others.

In some examples, the devices described herein (e.g., FIGS. 1A-D) can communicate with a remote server via an intermediary device 180 such as that shown in FIG. 1D. For instance, devices 1A-D can be configured to include a network interface communications capability as described in further detail below.

Figure 2:
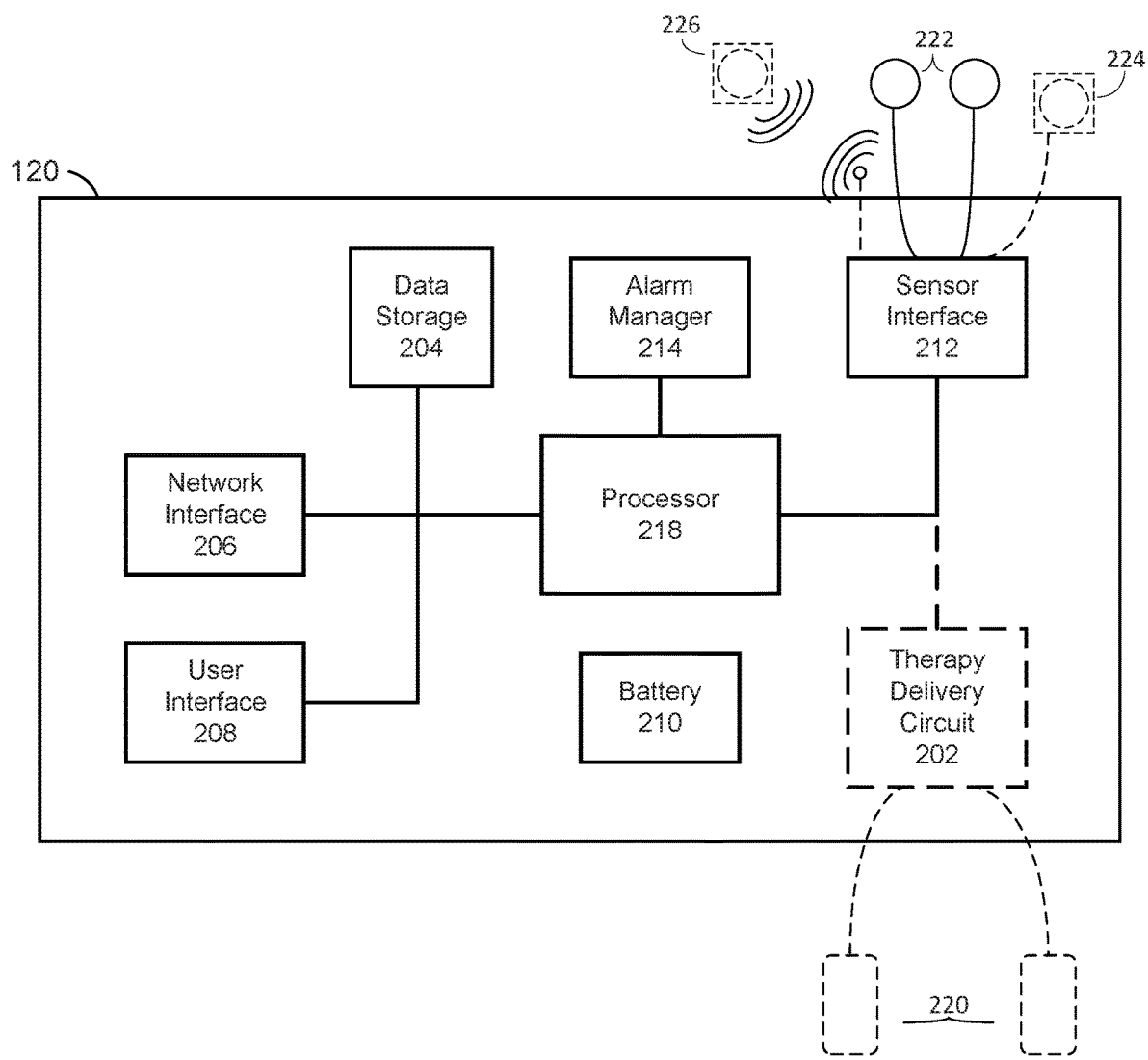
FIG. 2 depicts a schematic view of a sample controller for a wearable medical device such as that shown in FIG. 1, in accordance with an example of the present disclosure.

FIG. 2 illustrates a sample component-level view of the medical device controller 120. As shown in FIG. 2, the medical device controller 120 can include a therapy delivery circuitry 202, a data storage 204, a network interface 206, a user interface 208, at least one battery 210, a sensor interface 212, an alarm manager 214, and least one processor 218. A patient monitoring medical device can include a medical device controller 120 that includes like components as those described above but does not include the therapy delivery circuitry 202 (shown in dotted lines).

The therapy delivery circuitry 202 can be coupled to one or more electrodes 220 configured to provide therapy to the patient (e.g., therapy electrodes 114 as described above in connection with FIG. 1). For example, the therapy delivery circuitry 202 can include, or be operably connected to, circuitry components that are configured to generate and provide the therapeutic shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuitry and under control of one or more processors (e.g., processor 218) to provide, for example, at least one therapeutic shock to the patient including one or more pacing or defibrillation therapeutic pulses.

Pacing pulses can be used to treat cardiac arrhythmia conditions such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). In some examples, the capacitors can include a single film or electrolytic capacitor as a series connected device including a bank of the same capacitors. These capacitors can be switched into a series connection during discharge for a defibrillation pulse. For example, a single capacitor of approximately 140 uF or larger, or four capacitors of approximately 650 uF can be used. The capacitors can have a 1600 VDC or higher rating for a single capacitor, or a surge rating between approximately 350 to 500 VDC for paralleled capacitors and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuitry 202 can be configured to perform the switching and pulse delivery operations, e.g., under control of the processor 218. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

The data storage 204 can include one or more of non-transitory computer readable media, such as flash memory, solid state memory, magnetic memory, optical memory, cache memory, combinations thereof, and others. The data storage 204 can be configured to store executable instructions and data used for operation of the medical device controller 120. In certain examples, the data storage can include executable instructions that, when executed, are configured to cause the processor 218 to perform one or more operations.

In some examples, the network interface 206 can facilitate the communication of information between the medical device controller 120 and one or more other devices or entities over a communications network. For example, where the medical device controller 120 is included in an ambulatory medical device (such as medical device 100), the network interface 206 can be configured to communicate with a remote computing device such as a remote server or other similar computing device. The network interface 2206 can include communications circuitry for transmitting data in accordance with a Bluetooth® wireless standard for exchanging such data over short distances to an intermediary device (e.g., intermediary device 180 shown in FIG. 1D). For example, such an intermediary device can be configured as a base station, a "hotspot" device, a smartphone, a tablet, a portable computing device, and/or other devices in proximity of the wearable medical device 100. The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain examples, the user interface 208 can include one or more physical interface devices such as input devices, output devices, and combination input/output devices and a software stack configured to drive operation of the devices. These user interface elements can render visual, audio, and/or tactile content. Thus, the user interface 208 can receive input or provide output, thereby enabling a user to interact with the medical device controller 120.

The medical device controller 120 can also include at least one battery 210 configured to provide power to one or more components integrated in the medical device controller 120. The battery 210 can include a rechargeable multi-cell battery pack. In one example implementation, the battery 210 can include three or more 2200 mAh lithium ion cells that provide electrical power to the other device components within the medical device controller 120. For example, the battery 210 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 120.

The sensor interface 212 can include physiological signal circuitry that is coupled to one or more sensors configured to monitor one or more physiological parameters of the patient. As shown, the sensors can be coupled to the medical device controller 120 via a wired or wireless connection. The sensors can include one or more electrocardiogram (ECG) electrodes 222 (e.g., similar to sensing electrodes 112 as described above in connection with FIG. 1), vibration sensor 224, and tissue fluid monitors 226 (e.g., based on ultra-wide band radiofrequency devices).

The ECG electrodes 222 can monitor a patient's ECG information. For example, the ECG electrodes 222 can be galvanic (e.g., conductive) and/or capacitive electrodes configured to measure changes in a patient's electrophysiology to measure the patient's ECG information. The ECG electrodes 222 can transmit information descriptive of the ECG signals to the sensor interface 212 for subsequent analysis. For example, the sensor interface 212 can process a physiological signal received from the ECG electrodes to produce a physiological metric for the patient.

In certain implementations, the vibration sensors 224 be configured to detect cardiac or pulmonary vibration information. For example, the vibration sensors 224 can detect a patient's heart valve vibration information. For example, the vibration sensors 224 can be configured to detect cardio-vibrational signal values including any one or all of S1, S2, S3, and S4. From these cardio-vibrational signal values or heart vibration values, certain heart vibration metrics may be calculated, including any one or more of electromechanical activation time (EMAT), percentage of EMAT (% EMAT), systolic dysfunction index (SDI), and left ventricular systolic time (LVST). The vibration sensors 224 can also be configured to detect heart wall motion, for instance, by placement of the sensor in the region of the apical beat. The vibration sensors 224 can include a vibrational sensor configured to detect vibrations from a subject's cardiac and pulmonary system and provide an output signal responsive to the detected vibrations of a targeted organ, for example, being able to detect vibrations generated in the trachea or lungs due to the flow of air during breathing. In certain implementations, additional physiological information can be determined from pulmonary-vibrational signals such as, for example, lung vibration characteristics based on sounds produced within the lungs (e.g., stridor, crackle, etc.). The vibration sensors 224 can also include a multi-channel accelerometer, for example, a three-channel accelerometer configured to sense movement in each of three orthogonal axes such that patient movement/body position can be detected and correlated to detected cardio-vibrations information. The vibration sensors 224 can transmit information descriptive of the cardio-vibrations information to the sensor interface 212 for subsequent analysis.

The tissue fluid monitors 226 can use radio frequency (RF) based techniques to assess fluid levels and accumulation in a patient's body tissue. For example, the tissue fluid monitors 226 can be configured to measure fluid content in the lungs, typically for diagnosis and follow-up of pulmonary edema or lung congestion in heart failure patients. The tissue fluid monitors 226 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 226 can transmit information descriptive of the tissue fluid levels to the sensor interface 212 for subsequent analysis.

The sensor interface 212 can be coupled to any one or combination of sensing electrodes/other sensors to receive other patient data indicative of patient parameters. Once data from the sensors has been received by the sensor interface 212, the data can be directed by the processor 218 to an appropriate component within the medical device controller 120. For example, if heart data is collected by vibration sensor 224 and transmitted to the sensor interface 212, the sensor interface 212 can transmit the data to the processor 218 which, in turn, relays the data to a cardiac event detector. The cardiac event data can also be stored on the data storage 204.

In certain implementations, the alarm manager 214 can be configured to manage alarm profiles and notify one or more intended recipients of events specified within the alarm profiles as being of interest to the intended recipients. These intended recipients can include external entities such as users (patients, physicians, and monitoring personnel) as well as computer systems (monitoring systems or emergency response systems). The alarm manager 214 can be implemented using hardware or a combination of hardware and software. For instance, in some examples, the alarm manager 214 can be implemented as a software component that is stored within the data storage 204 and executed by the processor 218. In this example, the instructions included in the alarm manager 214 can cause the processor 218 to configure alarm profiles and notify intended recipients using the alarm profiles. In other examples, alarm manager 214 can be an application-specific integrated circuit (ASIC) that is coupled to the processor 218 and configured to manage alarm profiles and notify intended recipients using alarms specified within the alarm profiles. Thus, examples of alarm manager 214 are not limited to a particular hardware or software implementation.

In some implementations, the processor 218 includes one or more processors (or one or more processor cores) that each are configured to perform a series of instructions that result in manipulated data and/or control the operation of the other components of the medical device controller 120. In some implementations, when executing a specific process (e.g., cardiac monitoring), the processor 218 can be configured to make specific logic-based determinations based on input data received, and be further configured to provide one or more outputs that can be used to control or otherwise inform subsequent processing to be carried out by the processor 218 and/or other processors or circuitry with which processor 218 is communicatively coupled. Thus, the processor 218 reacts to specific input stimulus in a specific way and generates a corresponding output based on that input stimulus. In some example cases, the processor 218 can proceed through a sequence of logical transitions in which various internal register states and/or other bit cell states internal or external to the processor 218 can be set to logic high or logic low. As referred to herein, the processor 218 can be configured to execute a function where software is stored in a data store coupled to the processor 218, the software being configured to cause the processor 218 to proceed through a sequence of various logic decisions that result in the function being executed. The various components that are described herein as being executable by the processor 218 can be implemented in various forms of specialized hardware, software, or a combination thereof. For example, the processor 218 can be a digital signal processor (DSP) such as a 24-bit DSP processor. The processor 218 can be a multi-core processor, e.g., having two or more processing cores. The processor 218 can be an Advanced RISC Machine (ARM) processor such as a 32-bit ARM processor or a 64-bit ARM processor. The processor 218 can execute an embedded operating system, and include services provided by the operating system that can be used for file system manipulation, display & audio generation, basic networking, firewalling, data encryption and communications.

Example Battery Lock Features

Figure 3:
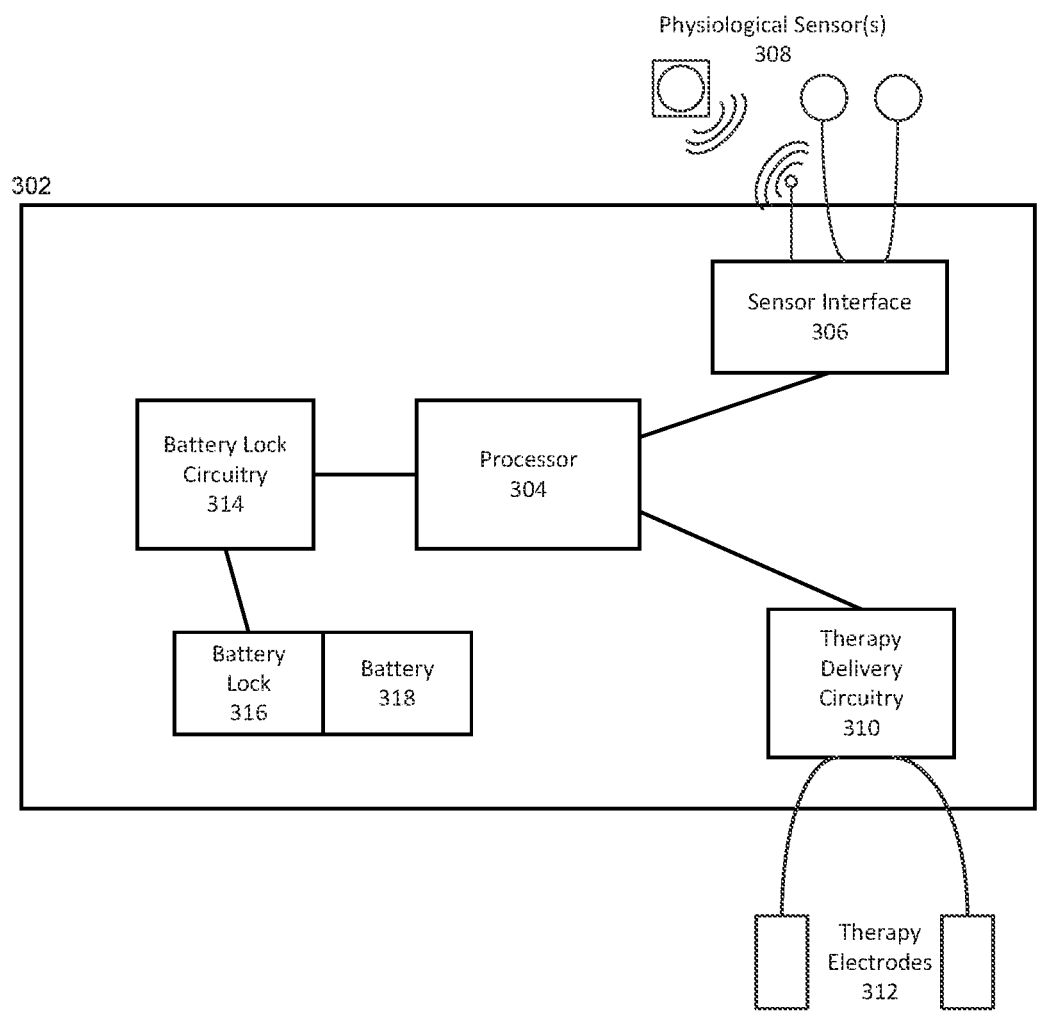
FIG. 3 depicts a schematic view of a controller for a wearable medical device including battery locking circuitry, in accordance with an example of the present disclosure.

As noted above, an ambulatory medical device such as a WCD can be designed to include battery locking elements. FIG. 3 illustrates an example medical device controller 302 (similar to medical device controller 120 as described above) that includes additional components for providing additional battery locking capability.

Similar to the controller 120, the controller 302 as shown in FIG. 3 can include a processor 304 configured to perform various operations, a sensor interface 306 operably connected to one or more physiological sensors 308, and a therapy delivery circuitry 310 operably connected to therapy electrodes 312. As further shown in FIG. 3, the controller 302 can also include a battery lock circuitry 314 operably connected to the processor 304. In certain implementations, the battery lock circuitry 314 can be configured to receive device status information from the processor 304. For example, the battery lock circuitry 314 can receive an indication from the processor 304 that the controller 302 is operating in a battery lock period. For example, based upon the configuration of the ambulatory medical device, the battery lock period can include a period of time where the controller 302 is performing a critical operation. In certain implementations, critical operations can include, but are not limited to, monitoring an ECG signal for the patient before or after detection of an arrhythmia condition, delivering an alarm to the patient, preparing to deliver a treatment pulse, delivering a treatment pulse, and other similar functions critical to the overall operation of the ambulatory medical device. In some implementations, the battery lock period can include any time that the patient is wearing the ambulatory medical device and has not requested to unlock the battery.

As further shown in FIG. 3, the battery lock circuitry 314 can be operably connected to a battery lock 316. The battery lock 316 can be an electro-mechanical device such as a solenoid, a screw mechanism including, for example, a motor rotatably connected to a reciprocating shaft, a magnetic locking device, or another similar locking device. The battery lock 316 can be configured to lock the battery 318 in the controller 302 in response to a lock signal received from the battery lock circuitry 314 at the beginning of the lock period. At the conclusion of the lock period, the battery lock 316 can be further configured to unlock the battery 318 in response to an unlock signal received from the battery lock circuitry 314.

It should be noted that battery lock circuitry 314 is shown as a separate component in FIG. 3 by way of example only. In certain implementations, the functionality of the battery lock circuitry 314 can be integrated into processor 304, thereby reducing the overall number of components in controller 302. It should also be noted that various components shown in FIG. 2 and described as included in controller 120 can also be included in controller 302. These components can include data storage, an alarm manager, a network interface, a user interface, and other similar components configured to provide additional functionality to the controller 302.

Figure 4A:
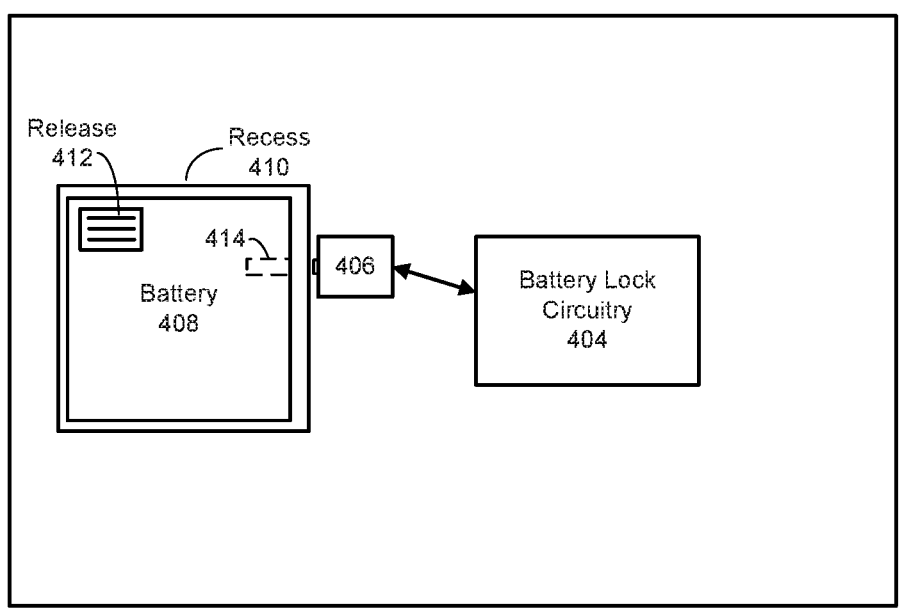
FIGS. 4A and 4B depict examples views of a battery locking mechanism, in accordance with an example of the present disclosure.
Figure 4B:
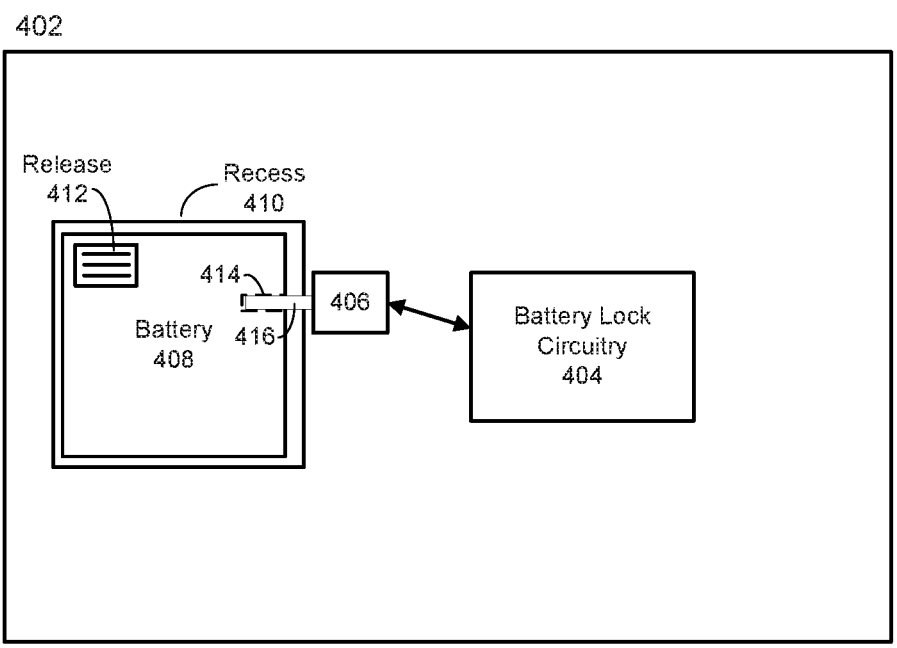

FIGS. 4A and 4B illustrated a more detailed view of a controller 402 that includes a battery in either a secondary unlocked (FIG. 4A) or secondary locked (FIG. 4B) configuration or manner. For example, as shown in FIG. 4A, a battery 408 can be placed within a battery recess 410 of the controller 402. As noted above, when inserting a battery into a controller for an ambulatory medical device, there can be an associated attachment/detachment mechanism such as a physical release. This arrangement provides a first locking configuration. However, as noted above, in certain situations this first locking configuration may not securely engage the battery. As shown in FIG. 4A, the battery 408 includes a release mechanism 412 configured to provide a means for disengaging the first locking manner of the battery within the recess 410. For example, the battery 408 can include a spring-loaded engagement feature that automatically depresses as the battery is inserted into the recess 410. Once the battery 408 is fully seated within the recess 410, the spring-loaded mechanism can return to its original position, thereby locking the battery into the recess in a first locking manner. In certain implementations, to release the battery 408 from the first locking manner, a person can depress or otherwise actuate the release mechanism 412 to manually depress the spring-loaded mechanism, thereby disengaging the first locking manner.

However, as noted above, in certain situations such as critical operational periods, it is desirable to have a second locking feature to further secure the battery in a second locking manner in the battery recess. As further shown in FIG. 4A, the controller 402 can further include battery lock circuitry 404 operably connected to a battery lock 406. The battery lock 406 can be configured to mechanically engage the battery 408 in a second locked state or manner upon receiving, for example, a lock signal from the battery lock circuitry 404.

As shown in FIG. 4B, in response to receiving the lock signal from the battery lock circuitry 404, the battery lock 406 can extend a solenoid shaft 416 into a recess 414 contained within the battery 408. Upon extension of the solenoid shaft 416, the battery 408 is secured in the battery recess 410 in a second locked manner. In certain implementations, the battery lock 406 can be configured to verify the position of the solenoid shaft 416 in the extended position and provide feedback to the battery lock circuitry 404. For example, the feedback can provide an indication that the solenoid shaft 416 has properly extended and the battery 408 is secured in the second locked manner.

Upon receiving an unlock signal from the battery lock circuitry 404, the battery lock 406 can withdraw the solenoid shaft 416 from the recess 414, thereby mechanically disengaging the battery 408 from the second locked manner as shown in FIG. 4A.

It should be noted that the components and the arrangement of those components as shown in FIGS. 4A and 4B are shown by way of example only. For instance, as noted above, a battery lock including an extending solenoid shaft is provided by way of example only. However, depending upon the design of the battery and controller, various other changes can be implemented. For example, in certain designs, the battery lock can be integrated into the battery. In such an arrangement, the battery can be configured to include one or more data lines. These data lines can be configured to operably connect to the battery lock circuitry when the battery is inserted into the battery recess. The battery lock circuitry can be configured to provide a lock signal to the battery lock integrated into the battery such that the battery lock engages a portion of the controller to secure the battery in the second locked manner.

As noted above, the battery locking period can be determined based upon various factors such as the programming of the ambulatory medical device and the medical application of the device. In certain implementations, the ambulatory medical device can be configured to operate in a normally locked mode or a normally unlocked mode. For example, in normally locked mode, the battery is locked in the second locked manner (e.g., where both first and second locked manners and/or mechanisms are engaged) anytime the ambulatory medical device is turned on and is being worn by a patient. In order to remove the battery, the patient may take off the device, turn the device off, or provide instructions via a user interface to release the battery from the second locked manner. Then, the patient can proceed to release the battery from the first locked manner.

Conversely, in normally unlocked mode, the battery is normally unlocked from the second locked manner unless the processor and/or the battery lock circuitry detects that the ambulatory medical device is performing a critical operation. Each of these modes is described in greater detail below in either FIG. 5 (normally locked) or FIG. 6 (normally unlocked).

Figure 5:
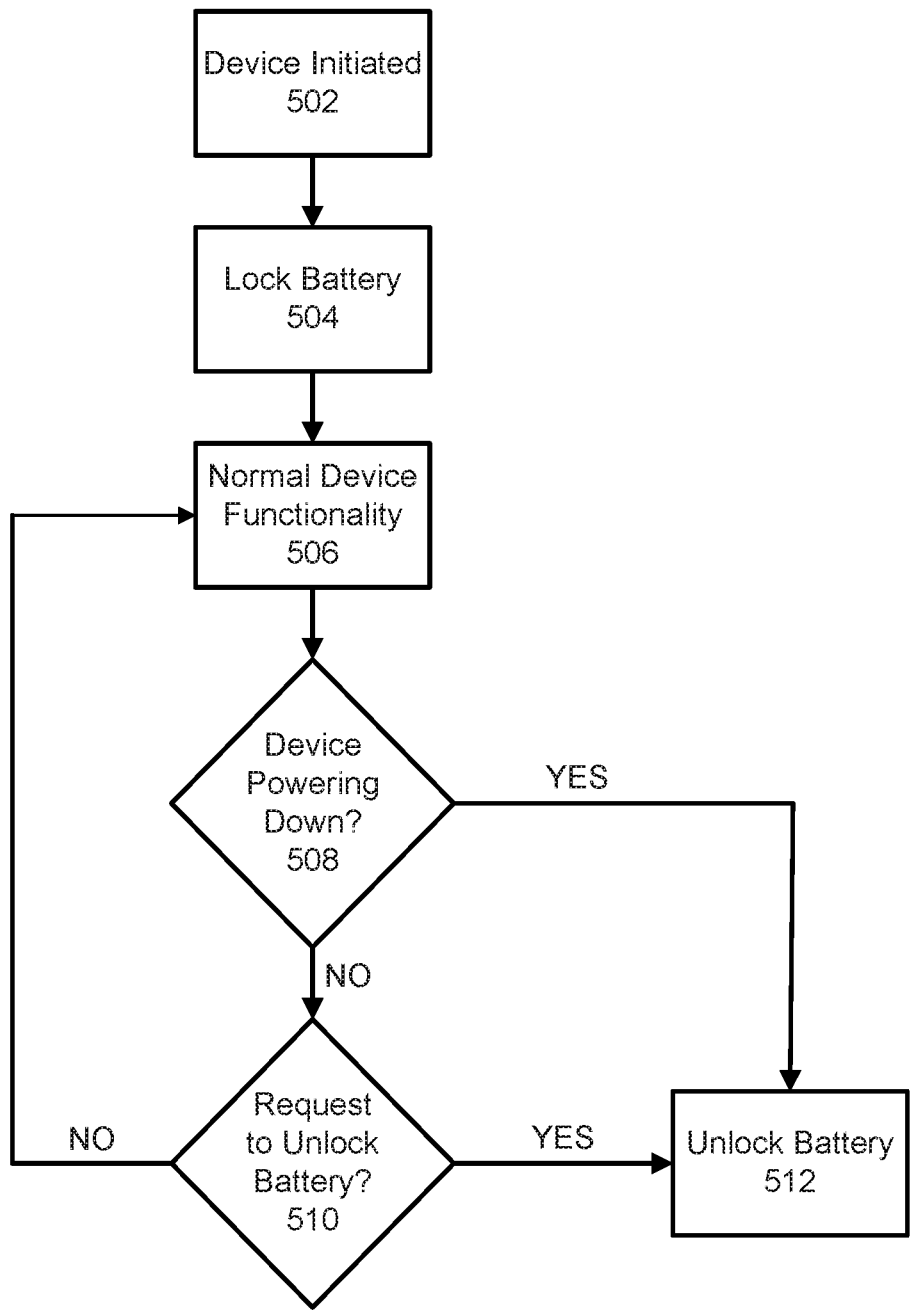
FIG. 5 depicts a sample process flow diagram illustrating a process for locking and unlocking a battery, in accordance with an example of the present disclosure.

Referring to FIG. 5, a process associated with the normally locked mode can begin when the ambulatory medical device is initiated 502. Initializing the device can include inserting a battery into the device, powering on the device, and/or otherwise turning the device on to perform its normal functionality. After initialization, a battery lock circuitry, such as battery lock circuitry 404 above, can provide a lock signal to a battery lock, such as battery lock 406 above. In response to the lock signal, the battery lock can lock 504 the battery into the device. In this state, the device can operate 506 its normal functionality. For example, if the device is a WCD, the device can monitor the patient's cardiac activity for any potential adverse cardiac events, provide treatment to any adverse cardiac events, report information such as heart monitoring information to a remote computing device, and perform other normal functions.

During normal operation, the processor can determine 508 whether the device is being powered down. For example, a user may access one or more options on a user interface to power off the device. If the processor determines 508 that the device is powering down, the battery lock circuitry can transmit an unlock signal to the battery lock. In response to the battery unlock signal, the battery lock can unlock 512 the battery such that the battery can be removed when the device is powered down.

In certain implementations, if the processor determines 508 that the device is not being powered down, the processor can further determine 510 if a user has requested to unlock the battery. For example, in certain implementations the user may not be able to turn the device off manually. Rather, the device automatically powers down when a user requests to replace the battery and automatically turns on when the battery is replaced. In such an implementation, the processor can determine 510 that the user has requested to unlock the battery and the battery is unlocked 512 as described above. For example, the device can include a user interface for providing one or more input options for a user. As shown in FIG. 7, a user can access an option to unlock the battery on the user interface. As shown in screenshot 702, the device can prompt the user for confirmation that they wish to remove the battery. If the user selects affirmatively, the device can prompt the user for additional information. For example, as shown in screenshot 704, the device can prompt the user for a secure pin. This added security step can act to decrease the likelihood that the battery is accidentally or carelessly released during operation of the device.

Referring again to FIG. 5, if the user has not requested to unlock the battery, the device can continue to perform 506 normal functions.

It should be noted that the process as shown in FIG. 5 is provided by way of example only. In certain implementations, various changes can be made to the arrangement of steps as shown in FIG. 5. For example, the ambulatory medical device can be configured such that the user cannot request that the battery be unlocked while the device is powered on. In such an arrangement, the processor determination 510 of an unlock request can be removed from the process flow. Additionally, the battery lock circuitry can be configured to respond to additional unlock triggering events such as a change to measured physiological metric, a caregiver input, and other similar triggering events.

Figure 6:
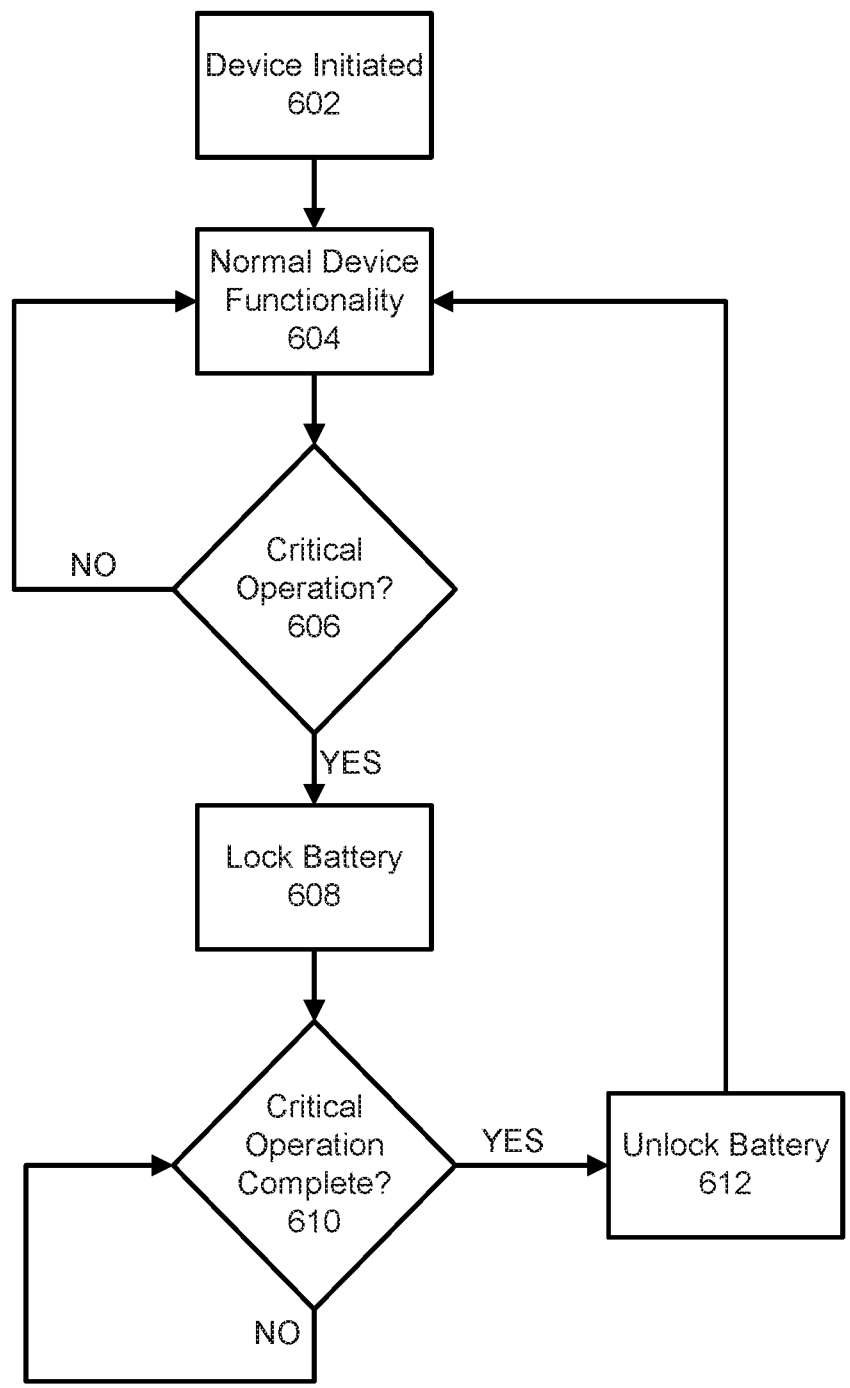
FIG. 6 depicts an alternate sample process flow diagram illustrating an alternate process for locking and unlocking a battery, in accordance with an example of the present disclosure.

Referring to FIG. 6, a process associated with the normally unlocked mode can begin when the ambulatory medical device is initiated 602. Initializing the device can include inserting a battery into the device, powering on the device, and/or otherwise turning the device on to perform its normal functionality. After initialization, the device can perform 604 its normal functionality. For example, if the device is a WCD, the device can monitor the patient's cardiac activity for any potential adverse cardiac events such as a cardiac arrhythmia, provide treatment to any adverse cardiac events, report information such as heart monitoring information to a remote computing device, and perform other normal functionality.

During normal functionality, the processor can determine 606 whether the device is entering a period of critical operation. For example, critical operations can include a set of functions included in the device's normal functionality. In some examples, critical operations can include, but are not limited to, monitoring an ECG signal of the patient, detecting and/or recording a cardiac arrhythmia, delivering an alarm to the patient, preparing to deliver a treatment pulse, delivering a treatment pulse, and other similar functions critical to the overall operation of the ambulatory medical device. For example, where the device is a cardiac monitor and such monitor has detected an atrial fibrillation onset event, the processor 606 may deem that the device has entered a period of critical operation. The period of critical operation may persist until an atrial fibrillation offset event is detected. Such a period can last anywhere from a few seconds (e.g., 3-60 seconds), a few minutes (e.g. 1-5 minutes), several minutes (e.g., 5-30 minutes), to longer durations such as a half hour, 1 hour, 2 hours, or several hours (e.g., 3-24 hours). Further, if the processor deems that the period of critical operation should last over a long period, in some implementations, the processor can switch to operate in a normally locked mode (as described in connection with FIG. 5 above).

If the processor does not determine 606 that the device is in a period of critical operation, the device can continue to perform 604 normal functionality. However, if the processor does determine 606 that the device is in a period of critical operation, the processor can provide an indication of the critical period of operation to the battery lock circuitry. The battery lock circuitry can transmit a lock signal to the battery lock in response to the indication of the critical period of operation, and the battery lock can lock 608 the battery.

The processor can determine 610 if the critical operation is complete. If the operation is not complete, the battery can remain locked. If the processor determines 610 that the critical operation is complete, the battery can unlock 612 as described above and the device can perform 604 normal functionality.

It should be noted that the process as shown in FIG. 6 is provided by way of example only. In certain implementations, various changes can be made to the arrangement of steps as shown in FIG. 6. For example, the ambulatory medical device can be configured such that the user can override the battery lock even during a critical operation.

Additional examples of where the processor may determine that the device is in a period of critical operation as provided below.

Sample Bradycardia Criterion:

ONSET: When the patient's average heart rate as detected via RF (calculated over e.g., 20 beats or over 30 seconds) drops below a predetermined, configurable threshold (e.g., 40 beats per minute) the system can report that the patient has entered bradycardia. For example, the threshold may be configured in a range from 20 to 60 beats per minute, with 40 being a default value. At this point, the processor may flag that the period of critical operation has begun and thereby engage the battery in the second locked manner.

OFFSET: When the patient is in Bradycardia and the patient's average heart rate (calculated over e.g., 20 beats or over 30 seconds) rises above a predetermined, configurable threshold (e.g., 40 beats per minute), the system can report that the patient has exited Bradycardia. For example, the threshold may be configured in a range from 20 to 60 beats per minute, with 45 being a default value. At this point, the processor may flag that the period of critical operation has ended and thereby dis-engage the battery from the second locked manner and/or mechanism.

Sample Tachycardia Criterion:

ONSET: When the patient's average heart rate (calculated over, e.g. 20 beats or 30 seconds) rises ABOVE a predetermined, configurable value (e.g., 100-250, default of 130), the system will report that the patient has entered Tachycardia. At this point, the processor may flag that the period of critical operation has begun and thereby engage the battery in the second locked manner.

OFSET: When the patient is in Tachycardia and the patient's average heart rate (calculated over, e.g. 20 beats or 30 seconds) drops BELOW a predetermined, configurable value (e.g., 100-250, default of 110), the system will report that the patient has exited Tachycardia. At this point, the processor may flag that the period of critical operation has ended and thereby dis-engage the battery from the second locked manner and/or mechanism.

Sample Heart Pause Criterion:

The patient must experience a cardiac pause with a duration greater than a duration set by a predetermined, configurable parameter (e.g., 1500-150000 ms, with a default setting of 3000 ms) before the processor will report the event. When the event is detected and/or reported, the processor may flag that the period of critical operation has begun and thereby engage the battery in the second locked manner.

Sample Atrial Fibrillation Duration Criteria:

For example, the processor can implement a process whereby the patient may remain in atrial fibrillation for longer than a duration set by a predetermined, configurable parameter (e.g., 0-60 minutes, default of 5 minutes) before the processor will report the AF event. Further, the patient may remain out of AF for longer than this duration for an AF offset event to be reported. When the AF onset event is detected and/or reported, the processor may flag that the period of critical operation has begun and thereby engage the battery in the second locked manner. When the AF offset event is detected and/or reported, the processor may flag that the period of critical operation has ended and thereby dis-engage the battery from the second locked manner and/or mechanism. Further, in some implementations, if the AF duration parameter is set to "NA" or "0", the processor can be configured to disable the arrhythmia duration feature and AF events can be reported as soon as they are detected. When the AF event is detected and/or reported, the processor may flag that the period of critical operation has begun and thereby engage the battery in the second locked manner.

Sensor Features

As noted above, an ambulatory medical device controller can include additional sensors such as motion sensors and environmental sensors. In certain implementations, these additional sensors can provide signals that impact whether the battery lock circuitry transmits a lock or unlock signal. For example, FIG. 8A illustrates an example medical device controller 802 (similar to medical device controller 302 as described above) that includes additional sensor components.

Figure 8A:
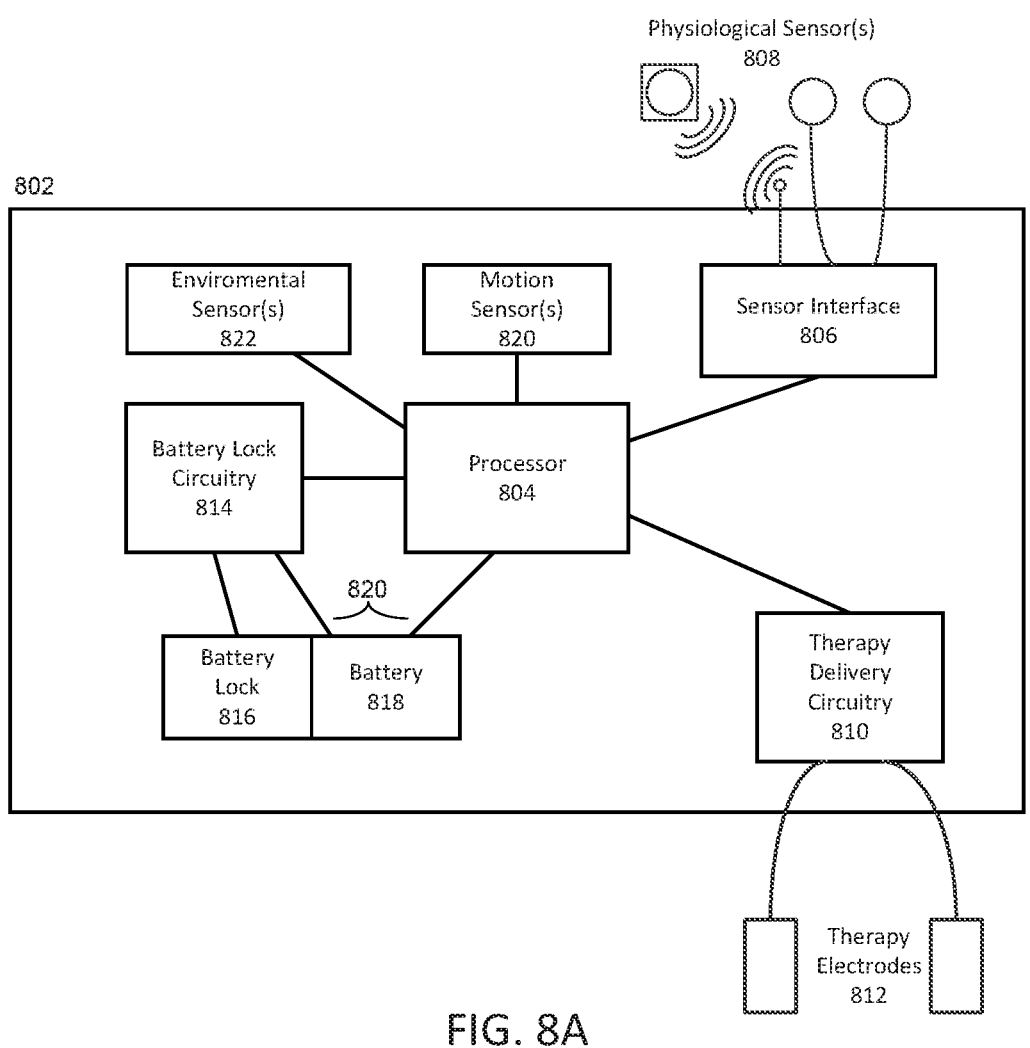
FIG. 8A depicts a schematic view of a controller including additional circuitry components, in accordance with an example of the present disclosure.

Like controller 302 above, the controller 802 as shown in FIG. 8A can include a processor 804 configured to perform various operations, a sensor interface 806 operably connected to one or more physiological sensors 808, a therapy delivery circuitry 810 operably connected to therapy electrodes 812, battery lock circuitry 814, a battery lock 816, and a battery 818. As further shown in FIG. 8A, the controller 802 can further include one or more motion sensors 820 and one or more environmental sensors 822.

Figure 8B:
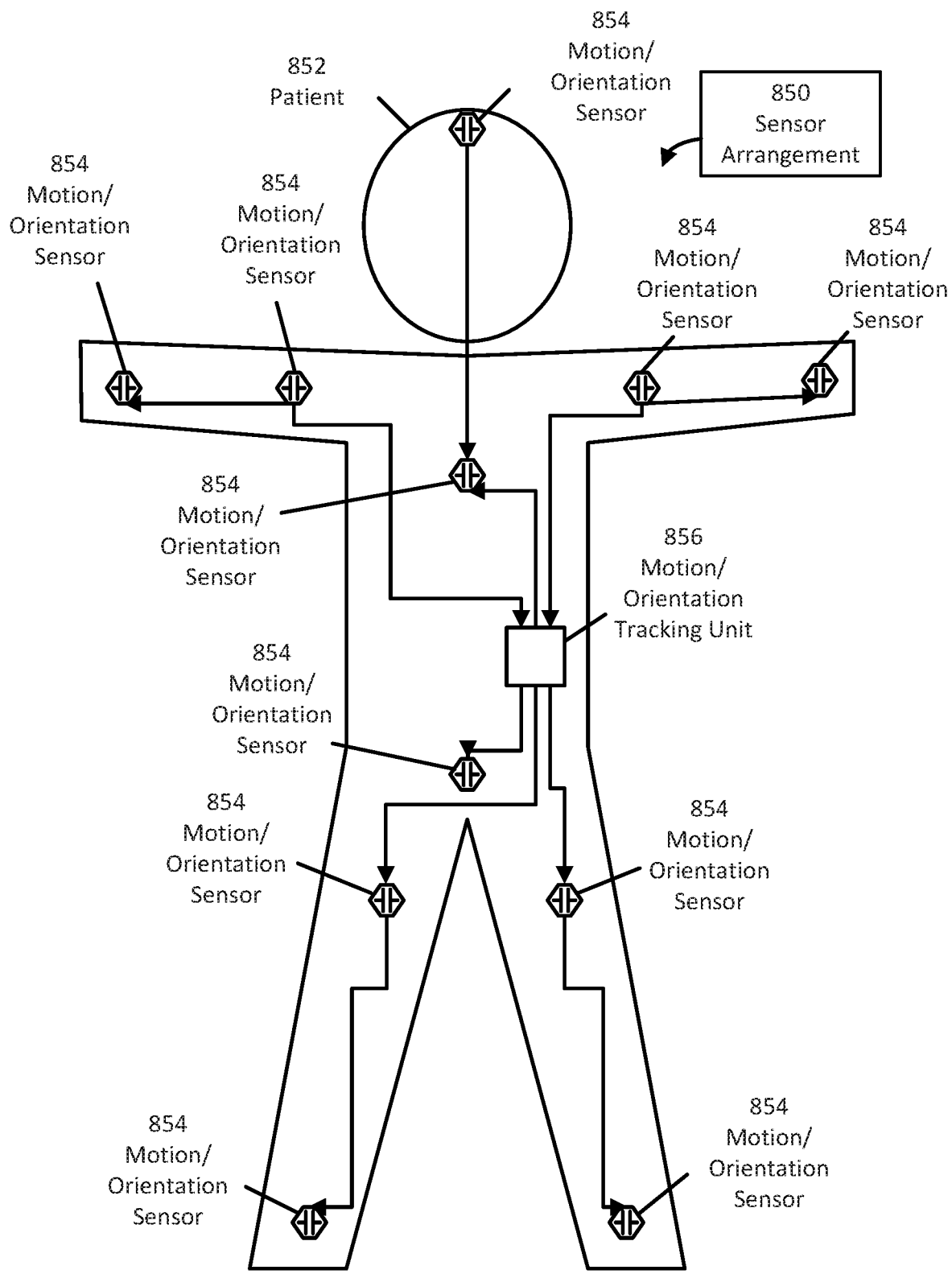
FIG. 8B depicts a schematic illustration of a sensor arrangement disposed proximate to a patient, in accordance with an example of the present disclosure.

In certain implementations, the motion sensor 820 can include a three-axis accelerometer configured to measure patient movement. For example, the motion sensor 820 can be configured to produce a motion signal that is indicative of patient movement. In certain implementations, the motion signal can indicate a fall event or the beginning or end of a period of physical activity for the patient (e.g., exercising). While FIG. 8A shows the motion sensor 820 within the controller 802, in some implementations, the motion sensor can be positioned on other locations on the patient's body. For example, referring to FIG. 8B, an example sensor arrangement 850 shown includes a plurality of motion/orientation sensors 854 and a motion tracking unit 856, all of which are attached to or worn by the patient 852.

The motion/orientation sensors 854 of the sensor arrangement 850 can include one or more inertial motion unit sensors ("IMU") including, but not limited to, one or more of one-dimensional accelerometers, two-dimensional accelerometers, three-dimensional accelerometers, gyroscopes, and magnetometers. For instance, examples of motion/orientation sensors 854 include multi-axis accelerometers and multi-axis gyroscopes, such as the ADIS16362iSensor® inertial system from ANALOG DEVICES®, or the iNEMO® M1 motion sensing system manufactured by STMicroelectronics® (which also includes a multi-axis magnetometer). Another example motion/orientation sensor 854 includes the MMA7361LC±1.5 g, ±6 g Three Axis Low-g Micromachined Accelerometer from Freescale Semiconductor.

Computations of the data collected by the motion/orientation sensor 854 are performed by a microprocessor and associated circuitry (e.g., FPGA, ASIC, and/or other electronic circuitry under control of the microprocessor) disposed within the motion/orientation sensor 854 itself, or a microprocessor in communication with the motion/orientation sensor 854 that is disposed elsewhere. Using data collected by the motion/orientation sensor 854 (e.g., linear acceleration, force, and/or orientation), the microprocessor determines the location and orientation of the motion/orientation sensor 854 in three-dimensional space.

Generally, one or more IMUs can measure a change in position of the portion of the patient's body in at least three axes: pitch (up/down relative to a transverse plane), yaw (left/right relative to a sagittal plane) and roll (clockwise/counter-clockwise relative to the frontal plane, e.g., in a posterior direction or an anterior direction). Each of the measurements in these axes result in the one or more IMUs generating a series of motion parameters corresponding to the portion of the patient's body to which the one or more IMUs is attached. For example, for each of six degrees of freedom (such as x, y, z and θx, θy and θz), an IMU can integrate over time a sensed acceleration, together with an estimate of gravity, to calculate a current velocity. Then the IMU can integrates the velocity to calculate a current position. Based on the position information, the IMU can derive one or more orientation parameters for the portion of the patient's body to use in the motion recognition/classification process.

Depending on the type of sensor used for the motion/orientation sensors 854, motion, including orientation in one or more dimensions of three-dimensional space (i.e., in x, y, and z directions of a Cartesian coordinate system) is detected. Data corresponding to the motion (whether acceleration data, orientation data, or other measurement data) is detected by the motion/orientation sensors 854 and provided to the motion tracking unit 856. The data can also indicate no motion (i.e., that the patient is not moving). Furthermore, an identifier (ID) corresponding to each sensor providing data is sent to the motion tracking unit, as is a time of detection. These data are then used to classify the motion as for example, the "patient is falling." Other types of patient motion that some examples are configured to detect and address include seizures, shivering, coughing, disoriented movement, movement associated with regaining of consciousness, sleepwalking, stumbling, and swooning.

In the example sensor arrangement 850 shown, the motion/orientation sensors 854 are connected to one another serially along separate paths terminating at extremities of the patient 852. As shown, these various example connection paths originate at the motion tracking unit 856. One path connects several sensors along a first path terminating at a right arm of the patient 852. Another path connects several sensors along a second path terminating at a crown of the skull of the patient 852. Other analogous paths extend to the left arm of the patient 852, and the right and left legs of the patient 852. Other paths may connect one or more sensors disposed at other portions of the body of the patient 852 to the motion tracking unit 856, as needed. Additionally, some examples may omit some of the sensors 854.

Referring again to FIG. 8A, based upon the motion signal indicative of patient movement, the processor 804 and/or the battery lock circuitry 814 can transmit a lock or unlock signal. For example, if the motion signal indicates a patient fall event has begun, the battery lock circuitry 814 can transmit a battery lock signal to the battery lock 816, thereby reducing the risk that the battery can become dislodged during the fall event. When the motion signal indicates that the fall event has finished, the battery lock circuitry 814 can transmit a battery unlock signal. Similarly, for a period of physical activity, the battery lock circuitry 814 can transmit the lock signal at the beginning of the physical activity (as determined from the motion signal) and transmit the unlock signal at the end of the physical activity.

Figure 9A:
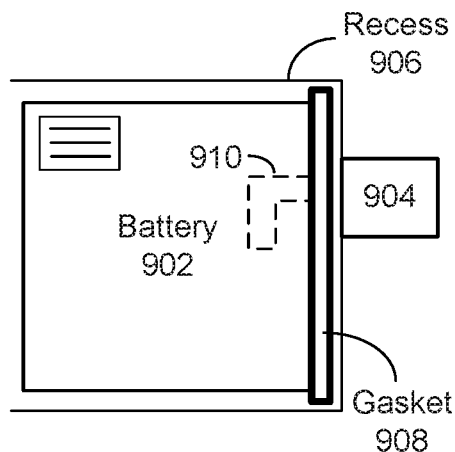
FIGS. 9A and 9B depict a battery locking mechanism including a sealing gasket, in accordance with an example of the present disclosure.
Figure 9B:
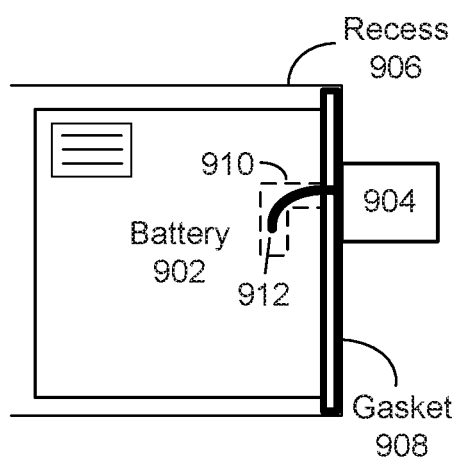

In some implementations, the environmental sensor 822 can include a moisture sensor configured to determine whether there is water or another similar fluid in close proximity to the controller 802. The moisture sensor can output a moisture signal that indicates a fluid level. The battery lock circuitry can be configured to transmit either the lock/unlock signal in response to the moisture signal. In some examples, an ambulatory medical device can include one or more sealing mechanisms configured to protect the device from water ingress. For example, the sealing mechanisms can include an actuatable gasket configured to be engaged to seal one or more water sensitive portions of the device. For example, as shown in FIGS. 9A and 9B, a battery 902 can be inserted into battery recess 906 until the battery abuts a gasket 908. As shown in FIG. 9A, when the battery lock 904 is not engaged with recess 910 in battery 902, the gasket can be in a relaxed state. However, when battery lock 904 extends curved shaft 912 as shown in FIG. 9B, the curve of the shaft, in concert with the shape of recess 910 causes battery 902 to exert a compressive force on gasket 908. The compressive force can deform or otherwise actuate the gasket 908 to form a watertight seal between the battery 902 and the recess 906, thereby preventing water ingress around the battery and into the internal components of the ambulatory medical device through the recess.

It should be noted that an actuated gasket is shown between the battery 902 and the recess 906 by way of example only. Additional gaskets can be included in various other portions of the ambulatory medical device where it is advantageous to prevent water ingress. A similar actuation method as the battery lock 904 and curved shaft 912 can be used to actuate the additional gaskets. It should also be noted that curved shaft 913 and recess 910 are shown by way of example as a means of exerting a pulling force on the battery 902. Additional actuation mechanisms such as a screw configured to pull the battery 902 into the recess 906 could be used as well.

Referring again to FIG. 8A, in certain implementations the environmental sensor 822 can also include a humidity sensor. For example, the environmental sensor 822 can include a HIH-4000 humidity sensor manufactured by Honeywell Sensing and Control (Golden Valley, Minn.), a division of Honeywell International, Inc. (Morris Plains, N.J.). For example, humidity sensors as used herein may operate based on detecting changes that alter electrical currents or temperature in the air. In implementations, humidity sensors as used herein can be based on capacitive, resistive, and/or thermal mechanisms. Capacitive humidity sensors may be implemented with a thin piece of metal oxide between two electrodes. The metal oxide's electrical capacity changes with as a result in changes to relative humidity. Resistive humidity sensors may be implemented by using ions in salt to measure electrical impedance. As humidity changes, resistance on electrodes on either side of the salt changes as well. Thermal humidity sensors may be implemented using two thermal sensors that conduct electricity based upon the humidity of the surrounding air. One sensor may be encased in a control environment such as dry nitrogen while the other sensor is configured to measure ambient air. Outputs from both sensors can be used to measure the relative humidity.

The HIH-4000 humidity sensor as referenced above is a thermoset polymer capacitive sensing element with on-chip integrated signal conditioning. The HIH-4000 humidity sensor is configured to output a voltage signal that varies linearly in relation to relative humidity. For example, the relative humidity (RH) for the HIH-4000 humidity sensor can be calculated using the following equation:

$$RH = (V_{OUT}/(0.0062 V_{SUPPLY})) - 25.8$$

where $V_{OUT}$ is the output voltage of the HIH-4000 humidity sensor and $V_{SUPPLY}$ is the input voltage of the HIH-4000 humidity sensor.

Referring back to FIG. 8A, in certain implementations, the humidity sensor can be configured to output a humidity signal indicative of the humidity level of the air around the controller 802. If the humidity exceeds a certain threshold (e.g., 85%), or changes a certain percentage in a particular amount of time (e.g., a 25% change in less than 10 minutes), the humidity signal can indicate an oncoming thunderstorm or other similar event. Similar to above with the moisture sensor, the battery lock circuitry 814 can transmit a lock signal to the battery lock 816, thereby causing actuation of one or more gaskets to prevent water or moisture ingress into the controller 802.

As further shown in FIG. 8A, the battery 818 can be operably connected to the processor 804 and/or the battery lock circuitry 814 via one or more data lines 820. The processor 804 and/or the battery lock circuitry 814 can be configured to monitor a health status of the battery 818 as indicted by, for example, a battery condition status signal transmitted from battery 818 over the data lines 820. In certain implementations, the battery lock circuitry 814 can monitor the health status of the battery 818 and transmit a lock or unlock signal accordingly. For example, the ambulatory medical device can be configured to operate in a normally locked mode (i.e., the battery is locked when the device is turned on). The battery lock circuitry 814 can be configured to monitor the battery condition status signal related to operation of the battery 818 and, if the battery lock circuitry determines that the battery condition status signal indicates the battery is to be changed, the battery lock circuitry can transmit an unlock signal to the battery lock 816.

For example, the battery condition status signal can be indicative of one or more current properties of the battery 818. In certain implementations, the battery condition status signal can trigger, via the battery lock circuitry 814, an unlock signal if the battery condition status signal satisfies one or more criteria. For example, if the battery has a current charge below a certain threshold (e.g., if the current battery charge is below 5%) the battery condition status signal can trigger an unlock event. This can occur so that the battery does completely lose charge without unlocking. Other battery condition status measurements can include, for example, battery output current, results of a battery integrity test, and end of life occurrence. In certain implementations, if the battery output current falls below a certain threshold (e.g., below 20 mA) the battery condition status signal can trigger an unlock event. Similarly, if the battery has failed an integrity test or has reached end of life, the battery condition status signal can trigger an unlock event.

Figure 10:
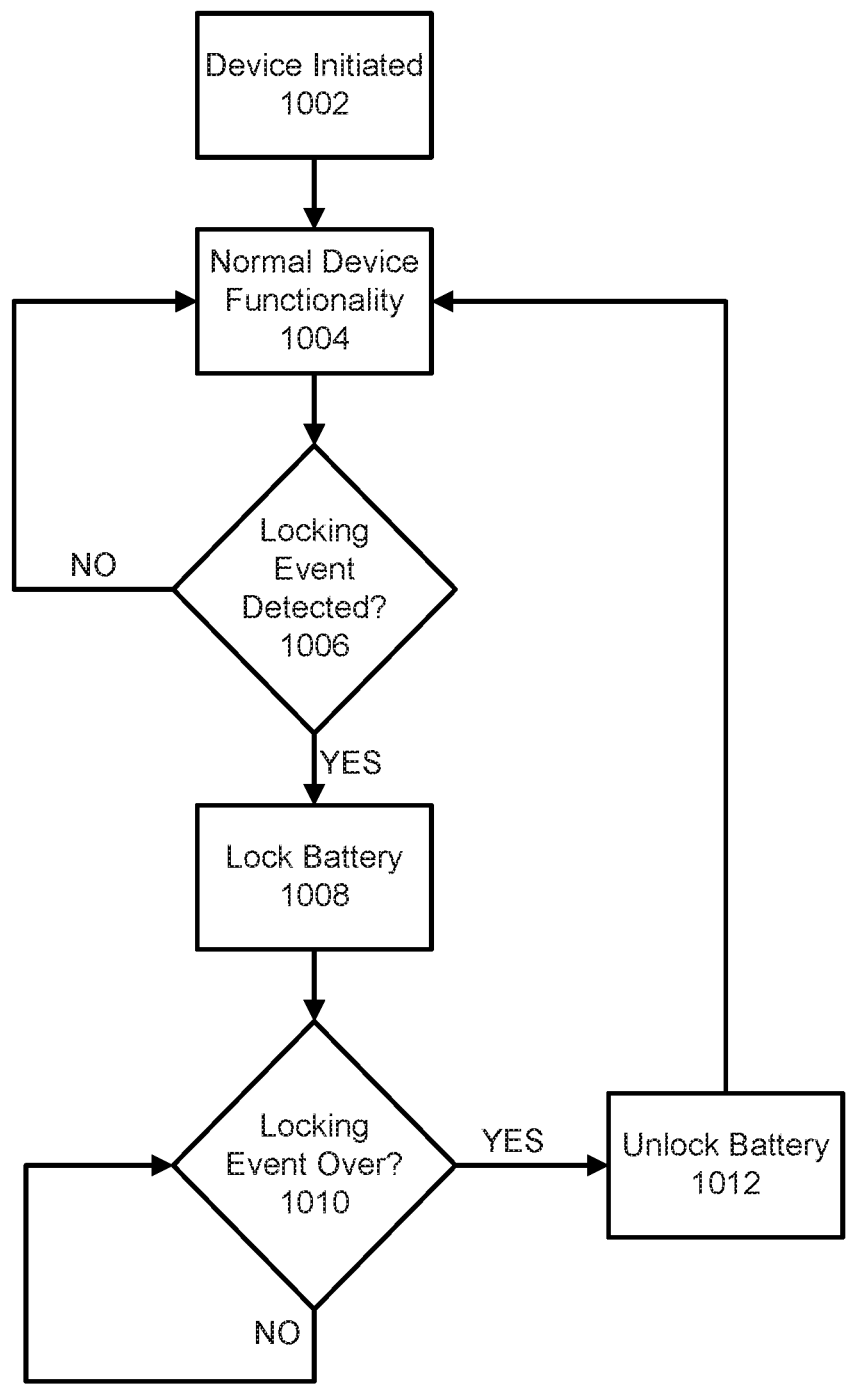
FIG. 10 depicts an alternate sample process flow illustrating an alternate process for locking and unlocking a battery, in accordance with an example of the present disclosure.

Referring to FIG. 10, signals produced by additional sensors such as the motion and environmental sensors as described above can trigger a lock/unlock signal. The process as shown in FIG. 10 can begin when the ambulatory medical device is initialized 1002. Initializing the device can include inserting a battery into the device, powering on the device, and/or otherwise turning the device on to perform its normal functionality. After initialization, the device can perform 1004 its normal functionality. For example, if the device is a WCD, the device can monitor the patient's cardiac activity for any potential adverse cardiac events, provide treatment to any adverse cardiac events, report information such as heart monitoring information to a remote computing device, and perform other normal functionality.

During normal functionality, a processor, such as processor 804 as described above, can determine 1006 whether a locking event has occurred. For example, a locking event can be determined 1006 based upon analysis of one or more signals received from various sensors. For example, the processor can analyze the moisture signal from a moisture sensor, a humidity signal from a humidity sensor, a motion sensor from an accelerometer, a battery health status signal, and various other signals. If the processor does not determine 1006 that that a locking event has occurred, the device can continue to perform 1004 normal functionality. However, if the processor does determine 1006 that a locking event has occurred, the processor can provide an indication of the locking event to a battery lock circuitry, such as battery lock circuitry 814 as described above. The battery lock circuitry can transmit a lock signal to a battery lock, such as battery lock 816 as described above, in response to the indication of the critical period of operation, and the battery lock can lock 1008 a battery, such as battery 818 as described above.

The processor can continue to monitor the output of the various sensors to determine 1010 if the locking event is over. If the locking event is not over, the battery can remain locked. If the processor determines 1010 that the locking event is over, the battery can unlock 1012 as described above and the device can continue to perform 1004 normal functionality.

It should be noted that the process as shown in FIG. 10 is provided by way of example only. In certain implementations, various changes can be made to the arrangement of steps as shown in FIG. 10. For example, the ambulatory medical device can be configured such that the user can override locking events caused by additional sensors such as motion and environmental sensors. It should also be noted that in each of process FIGS. 5, 6, and 10, normal device functionality can continue unaltered whether the battery is locked in the second locking manner or not. In certain implementations, the only interruption to non-critical normal device functionality can be starting a critical operational period as described herein.

As described herein, the battery locking processes and techniques can include an automated component such as the battery locks as described above to facilitate the second locking manner. However, it should be noted that such arrangements are provided by way of example only. In certain implementations, the second locking manner can be facilitated by an action initiated by the wearer or another similar user of the ambulatory medical device. For example, as shown in FIGS. 4A and 4B, the battery lock 406 can be implemented as a user-actuated locking mechanism that is actuated by, for example, pushing a button or sliding a switch that produces the movements of the solenoid shaft 416 into recess 414, thereby locking battery 408 in the second locking manner. To remove the battery 408, the wearer or similar user can perform a second action such as depressing the button again or sliding the switch in an opposite direction, thereby retracting the solenoid 416 into battery lock 406 and disengaging the second locking manner.

Figure 11A:
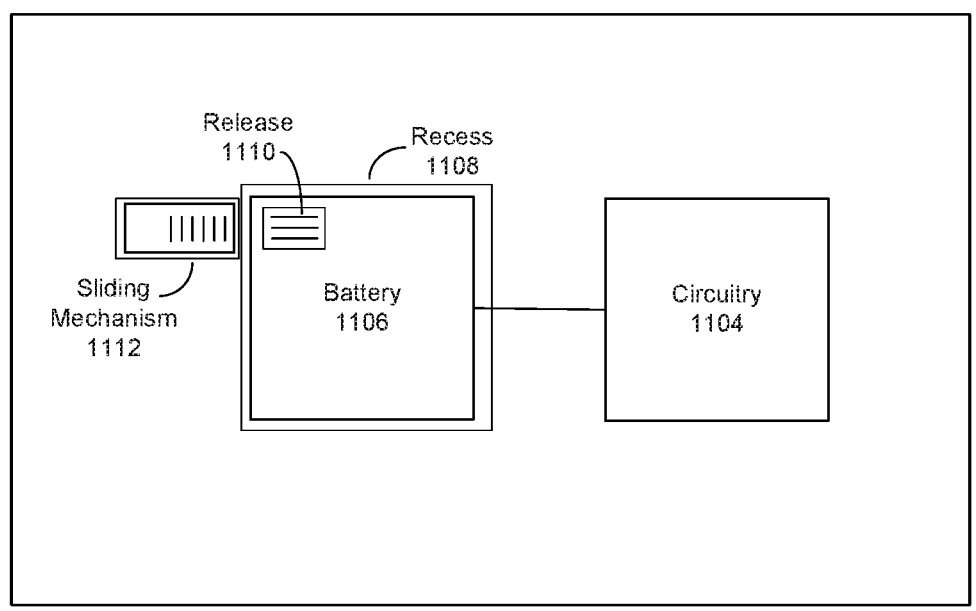
FIGS. 11A and 11B depict a battery locking mechanism including a sliding mechanism, in accordance with an example of the present disclosure.
Figure 11B:
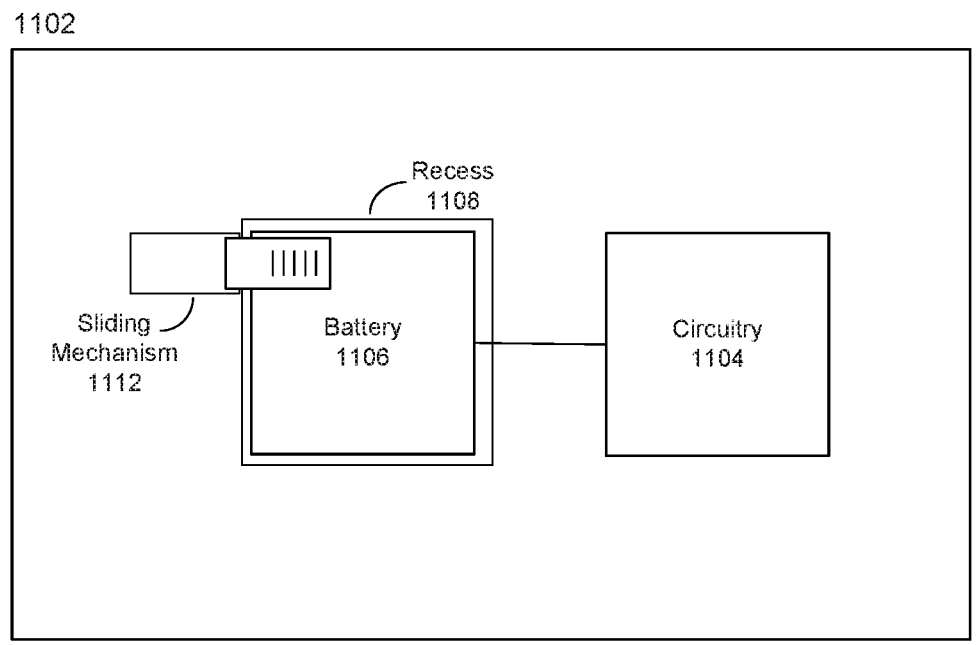

In certain implementations, a battery lock mechanism can be configured to cover a portion of the battery, or the battery release mechanism, thereby reducing the chance that a battery can become dislodged from an ambulatory medical device. For example, as shown in FIGS. 11A and 11B, a sliding mechanism can be included on an ambulatory medical device to providing a second locking manner for a battery. Similar to the examples as described above, an ambulatory medical device controller 1102 can house various circuitry 1104 related to the operation of the ambulatory medical device. The controller can further include a recess 1108 configured to receive a battery 1106. As shown in FIG. 11A, the battery 1106 can include a release mechanism 1110 configured to provide a means for disengaging a first locking manner of the battery within the recess 1108. For example, the battery 1106 can include a spring-loaded engagement feature that automatically depresses as the battery is inserted into the recess 1108. Once the battery 1106 is fully seated within the recess 1108, the spring-loaded mechanism can return to its original position, thereby locking the battery into the recess in a first locking manner. In certain implementations, to release the battery 1106 from the first locking manner, a person can depress or otherwise actuate the release mechanism 1110 to manually depress the spring-loaded mechanism, thereby disengaging the first locking manner.

However, as noted above, in certain situations it is desirable to have a second locking feature to further secure the battery in a second locking manner in the battery recess. As further shown in FIG. 11A, the controller 1102 can further include a sliding mechanism 1112 configured to cover at least a portion of the battery 1106 upon actuation of the sliding mechanism. For example, as shown in FIG. 11B, the sliding mechanism 1112 can be moved to an extended position where at least a portion of the sliding mechanism covers a portion of the battery 1106. In certain implementations, as shown in FIG. 11B, the sliding mechanism 1112 can be positioned such that, when extended, the sliding mechanism covers the release mechanism 1110, thereby preventing actuation of the release mechanism and removal of the battery 1106 from the battery recess 1108.

In certain implementations, the sliding mechanism 1112 can be user-actuated. For example, upon insertion of the battery 1106 into the battery recess 1108, a user such as the wearer of the ambulatory medical device can further actuate the sliding mechanism 1112 to move the sliding mechanism into the extended position as shown in FIG. 11B. In other examples, the sliding mechanism 1112 can be configured to extend automatically upon insertion of the battery 1106. For example, the sliding mechanism 1112 can include a tensioned spring that, upon insertion of the battery 1106, the tension is released, and the sliding mechanism moves into the extended position. In some examples, the sliding mechanism 1112 can be automatically actuated by, for example a battery lock as described above.

In certain implementations, a user can interact with the sliding mechanism 1112 to return the sliding mechanism to a retracted state such as that shown in FIG. 11A. For example, the user may have to perform a specific action such as depress the sliding mechanism 1112 and move the sliding mechanism away from the battery, thereby disengaging the second locking manner.

It should be noted that physical actuation of a sliding mechanism as described in reference to FIGS. 11A and 11B is provided by way of example only. Additional techniques for providing the sliding mechanism can be incorporated into a battery lock design. In certain implementations, an extending solenoid shaft can be used to provide actuation of a sliding mechanism or the movable component of the sliding mechanism itself.

It should be noted that, in the examples above, the ambulatory medical device is described as a WCD for discussion purposes only. However, the battery locking techniques and processes as described herein can be applied to other medical devices. For example, battery locking circuitry and a battery lock as described herein can be integrated into a cardiac monitoring device such that, when performing various operations such as recording a patient's ECG, the battery can be locked into the cardiac monitoring device, thereby providing for an accurate and complete ECG recording for the patient without risk of the battery becoming dislodged or otherwise removed from the device.

EXAMPLE SCENARIOS

In an example, a patient may have been prescribed an ambulatory medical device such as a WCD to wear for an extended period of time (e.g., 30 days). The patient may be elderly and have limited range of motion and, as such, may be prone to falling. The WCD can include battery lock components such as those described herein such that the battery is locked into the device in a second manner, thereby reducing any risk that the battery may become dislodged from the device if the patient falls.

In another example, a patient that has been prescribed a WCD may have had several false alarms in public places that have caused the patient unwanted attention and embarrassment. The patient may desire to simply remove the device's battery upon the next issuance of an alarm. However, using the battery locking techniques as described herein, the alarm is defined by the device as a critical operation and the battery is locked into the device. If the patient then needs treatment, the device is still operating normally. In conventional examples where the patient could remove an unlocked battery to prevent an alarm, the patient could experience an untreated adverse cardiac event.

In yet another example, a patient that has been prescribed a WCD lives in a tropical climate where there is humidity and high chances of random thunderstorms. By monitoring environmental factors such as humidity as described above, the device can lock the battery against a waterproof gasket to prevent any water ingress into the device.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the scope of the appended claims. For example, it is to be understood that the present disclosure contemplates that, to the extent possible, one or more features of any example can be combined with one or more features of any other example.

Other examples are within the spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. An ambulatory medical device configured to be worn by a patient, the device comprising:
   at least one physiological sensor configured to couple to the patient, wherein the at least one physiological sensor comprises an ECG sensor configured to detect one or more ECG signals of the patient;
   physiological signal circuitry operably connected to the at least one physiological sensor and configured to
     receive a physiological signal from the at least one physiological sensor, and
     produce a physiological metric based upon the received physiological signal, wherein the physiological metric comprises at least one ECG metric;
   therapy delivery circuitry configured to produce, based upon the physiological metric, a therapy shock;
   battery lock circuitry configured to
     transmit a lock signal at a beginning of a battery lock period of the ambulatory medical device, and
     transmit an unlock signal upon detecting an unlock triggering event indicating an end of the battery lock period of the ambulatory medical device;
   a battery being configured to be securely disposed within a chamber of the ambulatory medical device in a first locked manner and provide power to the ambulatory medical device; and
   a battery lock configured to
     mechanically engage the battery in a second locked manner upon receiving the lock signal indicating the beginning of the battery lock period of the ambulatory medical device, and
     mechanically disengage the battery from the second locked manner upon receiving the unlock signal signaling the end of the battery lock period.

2. The ambulatory medical device of claim 1, further comprising a motion sensor in communication with the battery lock circuitry and configured to produce a motion signal of the patient, wherein the battery lock circuitry is configured to transmit at least one of the lock signal and the unlock signal in response to the motion signal.

3. The ambulatory medical device of claim 2, wherein the motion signal indicates a patient fall event.

4. The ambulatory medical device of claim 3, wherein the battery lock circuitry is configured to determine the patient fall event based upon the motion signal transgressing a threshold value associated with a fall event.

5. The ambulatory medical device of claim 3, wherein the motion signal indicates an end of the patient fall event, and wherein the battery lock circuitry is further configured to transmit the unlock signal in response to the end of the patient fall event.

6. The ambulatory medical device of claim 2, wherein the motion signal indicates a beginning of a physical activity event and an end of the physical activity event.

7. The ambulatory medical device of claim 6, wherein the battery lock circuitry is further configured to:
   determine the beginning of the physical activity event and the end of the physical activity event from the motion signal;
   transmit the lock signal in response to the beginning of the physical activity event; and
   transmit the unlock signal in response to the end of the physical activity event.

8. The ambulatory medical device of claim 1, further comprising a humidity sensor in communication with the battery lock circuitry and configured to produce a humidity signal.

9. The ambulatory medical device of claim 8, wherein the battery lock circuitry is configured to transmit at least one of the lock signal and the unlock signal in response to the humidity signal.

10. The ambulatory medical device of claim 1, further comprising a moisture sensor in communication with the battery lock circuitry and configured to produce a moisture signal.

11. The ambulatory medical device of claim 10, wherein the battery lock circuitry is configured to transmit at least one of the lock signal and the unlock signal in response to the moisture signal.

12. The ambulatory medical device of claim 10, further comprising at least one sealing mechanism configured to protect the ambulatory medical device from water ingress.

13. The ambulatory medical device of claim 12, wherein the at least one sealing mechanism comprises an actuatable gasket configured to be engaged to seal one or more water-sensitive portions of the ambulatory medical device when the battery is in the second locked manner.

14. The ambulatory medical device of claim 1, wherein the battery lock circuitry is further configured to monitor a health status of the battery and transmit at least one of the lock signal and/or the unlock signal in response to the health status.

15. The ambulatory medical device of claim 14, wherein the battery lock circuitry is further configured to transmit the unlock signal in response to determining that the health status indicates that the battery satisfies at least one of: has a current charge that is below a charge threshold, is unable to output a current above a predetermined current threshold level, has failed a battery integrity test, and/or has reached end of life.

16. The ambulatory medical device of claim 1, wherein the unlock triggering event comprises at least one of a change in operation of the ambulatory medical device, a change to the physiological metric, a patient input, and/or a caregiver input.

17. The ambulatory medical device of claim 16, wherein the battery lock circuitry is further configured to transmit the unlock signal upon detecting an unlock triggering event indicating the end of the battery lock period of the ambulatory medical device and determining the ambulatory medical device is not operating in a critical operational period.

18. The ambulatory medical device of claim 1, wherein the battery lock comprises at least one of a solenoid, a motor rotatably connected to a reciprocating shaft, and/or a user-actuated locking mechanism.

19. The ambulatory medical device of claim 1, wherein the battery comprises at least one of the battery lock and/or a portion of the battery lock circuitry.

20. An ambulatory medical device to be worn by a patient, the device comprising:
   at least one physiological sensor configured to couple to the patient, wherein the at least one physiological sensor comprises an ECG sensor configured to detect one or more ECG signals of the patient;
   physiological signal circuitry operably connected to the at least one physiological sensor and configured to
      receive a physiological signal from the at least one physiological sensor, and
      produce a physiological metric based upon the received physiological signal, wherein the physiological metric comprises at least one ECG metric;
   therapy delivery circuitry configured to produce a therapy shock based upon the physiological metric;
   battery lock circuitry configured to
      transmit a lock signal at a beginning of a critical operational period of the ambulatory medical device, and
      transmit an unlock signal at an end of the critical operational period of the ambulatory medical device;
   a battery configured to be securely located within a chamber of the ambulatory medical device in a first secure manner and provide power to the ambulatory medical device; and
   a battery lock configured to
      mechanically engage the battery in a second secure manner upon receiving the lock signal indicating the beginning of the critical operational period of the ambulatory medical device, and
      mechanically disengage the battery from the second secure manner upon receiving the unlock signal signaling the end of the critical operational period.

21. The ambulatory medical device of claim 20, wherein the critical operational period comprises the therapy delivery circuitry delivering a therapy shock to the patient.

22. The ambulatory medical device of claim 20, wherein the critical operational period comprises an alarm output by the ambulatory medical device, the alarm indicative of a pending therapeutic shock.

23. The ambulatory medical device of claim 20, wherein the end of the critical operational period comprises at least one of a change in operation of the ambulatory medical device, a change to the physiological metric, a patient input, and/or a caregiver input.

24. The ambulatory medical device of claim 23, wherein the battery lock circuitry is further configured to transmit the unlock signal upon detecting an unlock triggering event indicating the end of the critical operational period of the ambulatory medical device.

25. The ambulatory medical device of claim 20, wherein the battery lock comprises at least one of a solenoid, a motor rotatably connected to a reciprocating shaft, and/or a user-actuated locking mechanism.

* * * * *